(12) United States Patent
Kluener et al.

(10) Patent No.: US 10,695,068 B2
(45) Date of Patent: Jun. 30, 2020

(54) HYSTERESIS REMOVAL FEATURE IN SURGICAL STAPLING INSTRUMENT

(71) Applicant: ETHICON LLC, Guaynabo, PR (US)

(72) Inventors: Joseph T. Kluener, Cincinnati, OH (US); Jeffrey C. Gagel, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 398 days.

(21) Appl. No.: 15/581,546

(22) Filed: Apr. 28, 2017

(65) Prior Publication Data

US 2018/0310938 A1 Nov. 1, 2018

(51) Int. Cl.
   *A61B 17/00*   (2006.01)
   *A61B 17/115*  (2006.01)
   *A61B 17/072*  (2006.01)
   *A61B 90/00*   (2016.01)

(52) U.S. Cl.
   CPC .... *A61B 17/1155* (2013.01); *A61B 17/07207* (2013.01); *A61B 2017/00398* (2013.01); *A61B 2017/00734* (2013.01); *A61B 2017/07257* (2013.01); *A61B 2017/07271* (2013.01); *A61B 2017/07285* (2013.01); *A61B 2090/061* (2016.02); *A61B 2090/0811* (2016.02)

(58) Field of Classification Search
   CPC .................................................. A61B 17/1155
   USPC ....................................................... 227/179.1
   See application file for complete search history.

(56) References Cited

U.S. PATENT DOCUMENTS

| | | | |
|---|---|---|---|
| 5,205,459 A | 4/1993 | Brinkerhoff et al. | |
| 5,271,544 A | 12/1993 | Fox et al. | |
| 5,275,322 A | 1/1994 | Wolf et al. | |
| 5,285,945 A | 2/1994 | Brinkerhoff et al. | |
| 5,292,053 A | 3/1994 | Smith et al. | |

(Continued)

FOREIGN PATENT DOCUMENTS

| | | |
|---|---|---|
| EP | 3 108 821 A2 | 12/2016 |
| WO | WO 2016/127433 A1 | 8/2016 |

OTHER PUBLICATIONS

European Search Report and Written Opinion dated Aug. 1, 2018 for Application No. EP 18169739.2, 10 pgs.

(Continued)

*Primary Examiner* — Chelsea E Stinson
(74) *Attorney, Agent, or Firm* — Frost Brown Todd LLC

(57) ABSTRACT

An apparatus includes a body, a shaft assembly, an end effector, and an indicator assembly. The end effector includes a stationary component and a movable component. The indicator assembly includes a translating member and an indicator member. The translating member translates relative to the body in response to movement of the movable component relative to the stationary component. The indicator member moves from a first position toward a second position. The indicator member includes an integral resilient feature configured to bias the indicator member toward the first position. The translating member drives the indicator member toward the second position in response to movement of the movable component relative to the stationary component in a first direction. The resilient feature drives the indicator member toward the first position in response to movement of the movable component relative to the stationary component in a second direction.

20 Claims, 26 Drawing Sheets

(56) References Cited

U.S. PATENT DOCUMENTS

| | | | |
|---|---|---|---|
| 5,333,773 | A | 8/1994 | Main et al. |
| 5,350,104 | A | 9/1994 | Main et al. |
| 5,533,661 | A | 7/1996 | Main et al. |
| 7,364,060 | B2 | 4/2008 | Milliman |
| 7,794,475 | B2 | 9/2010 | Hess et al. |
| 8,910,847 | B2 | 12/2014 | Nalagatla et al. |
| 9,289,207 | B2 | 3/2016 | Shelton |
| 9,463,022 | B2 | 10/2016 | Swayze et al. |
| 9,498,222 | B2 | 11/2016 | Scheib et al. |
| 9,532,783 | B2 | 1/2017 | Swayze et al. |
| 9,572,573 | B2 | 2/2017 | Scheib et al. |
| 9,597,081 | B2 | 3/2017 | Swayze et al. |
| 2014/0151430 | A1 | 6/2014 | Scheib et al. |
| 2014/0158747 | A1 | 6/2014 | Measamer et al. |
| 2015/0083772 | A1 | 3/2015 | Miller et al. |
| 2015/0083773 | A1 | 3/2015 | Measamer et al. |
| 2015/0083774 | A1 | 3/2015 | Measamer et al. |
| 2015/0083775 | A1 | 3/2015 | Leimbach et al. |
| 2016/0100837 | A1 | 4/2016 | Huang et al. |
| 2016/0374666 | A1 | 12/2016 | DiNardo et al. |
| 2016/0374667 | A1 | 12/2016 | Miller et al. |
| 2016/0374671 | A1* | 12/2016 | Measamer ............ A61B 17/068 227/175.1 |
| 2016/0374672 | A1 | 12/2016 | Bear et al. |
| 2017/0086848 | A1 | 3/2017 | Miller et al. |
| 2017/0258471 | A1* | 9/2017 | DiNardo .............. A61B 17/068 |

OTHER PUBLICATIONS

International Search Report and Written Opinion dated Aug. 1, 2018 for Application No. PCT/US2018/028128, 16 pgs.
U.S. Appl. No. 15/350,513, filed Nov. 14, 2016.
U.S. Appl. No. 15/581,640, filed Apr. 28, 2017.

\* cited by examiner

HYSTERESIS REMOVAL FEATURE IN SURGICAL STAPLING INSTRUMENT

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
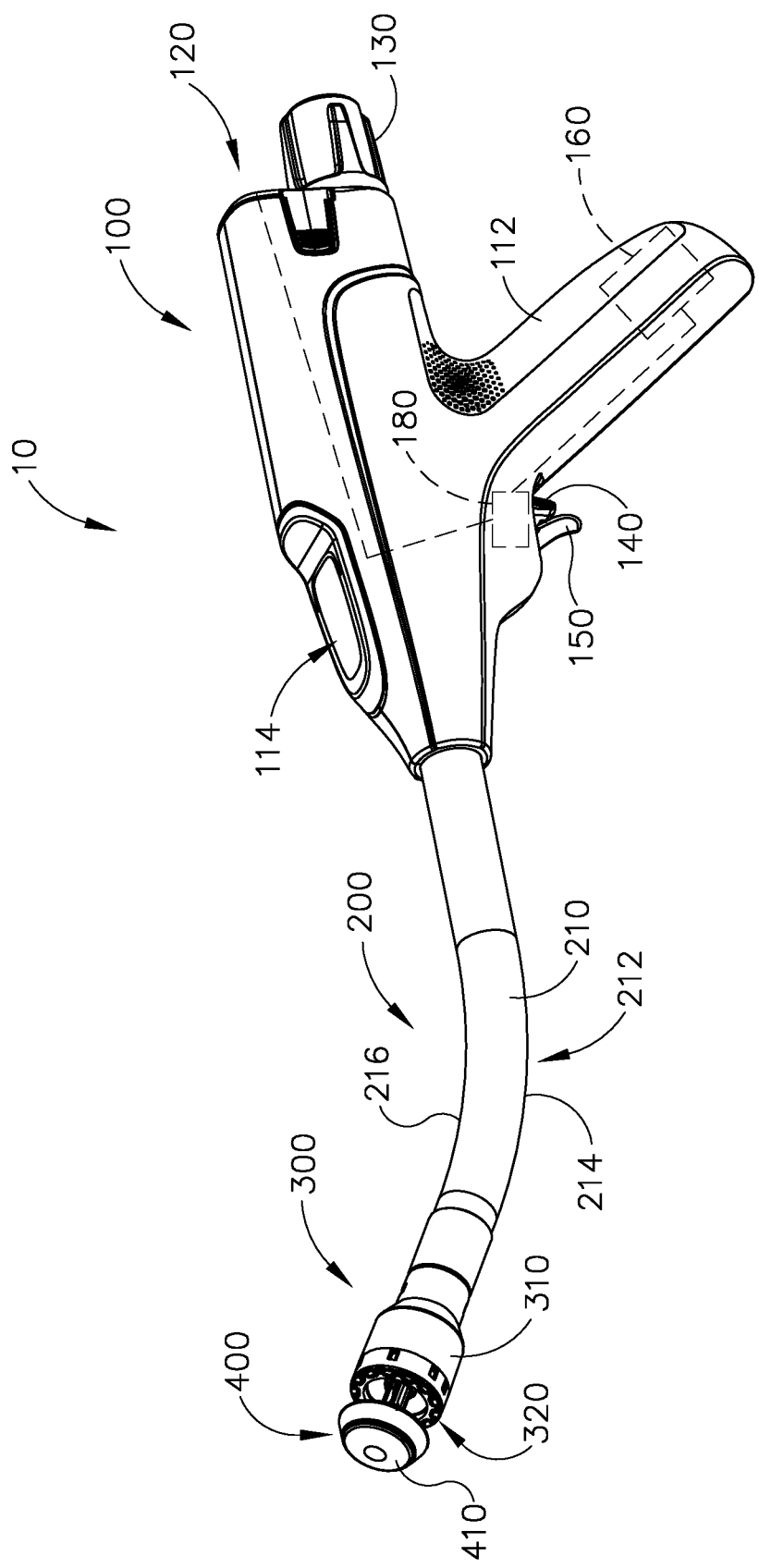
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
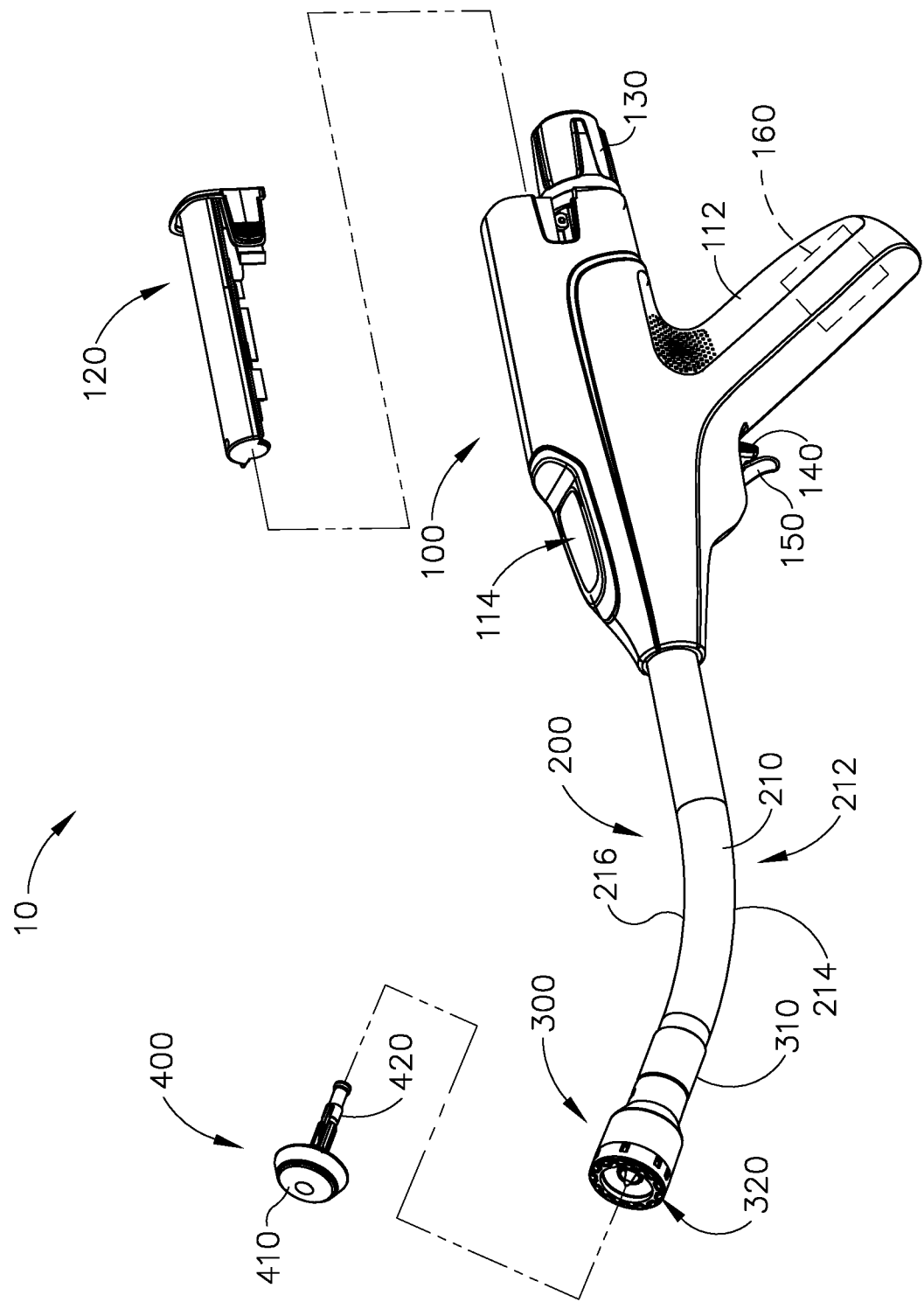
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), an anvil (400), and a removable battery pack (120). Each of these components will be described in greater detail below. It should be understood that, in addition to or in lieu of the following, instrument (10) may be further constructed and operable in accordance with at least some of the teachings of U.S. Pub. No. 2016/0374672, entitled "Method of Applying an Annular Array of Staples to Tissue," published Dec. 29, 2016, issued as U.S. Pat. No. 10,478,189 on Nov. 19, 2019; U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

A. Exemplary Tissue Engagement Features of Circular Stapling Instrument

Figure 3:
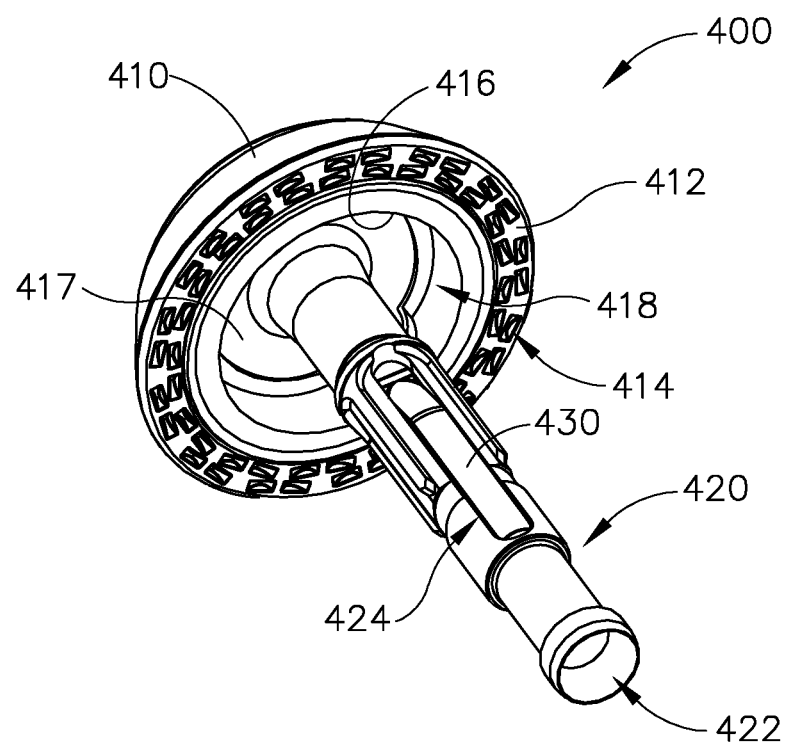
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. Staple forming pockets (414) are configured to deform staples as the staples are driven into staple forming pockets (414) (e.g., deforming a generally "U" shaped staple into a "B" shape as is known in the art). Shank (420) defines a bore or lumen (422) and includes a pair of pivoting latch members (430) positioned in bore (422). Each latch member (430) includes features that allows anvil (400) to be removably secured to a trocar (330) of stapling head assembly (300) as will be described in greater detail below. It should be understood, however, that anvil (400) may be removably secured to a trocar (330) using any other suitable components, features, or techniques.

Figure 4:
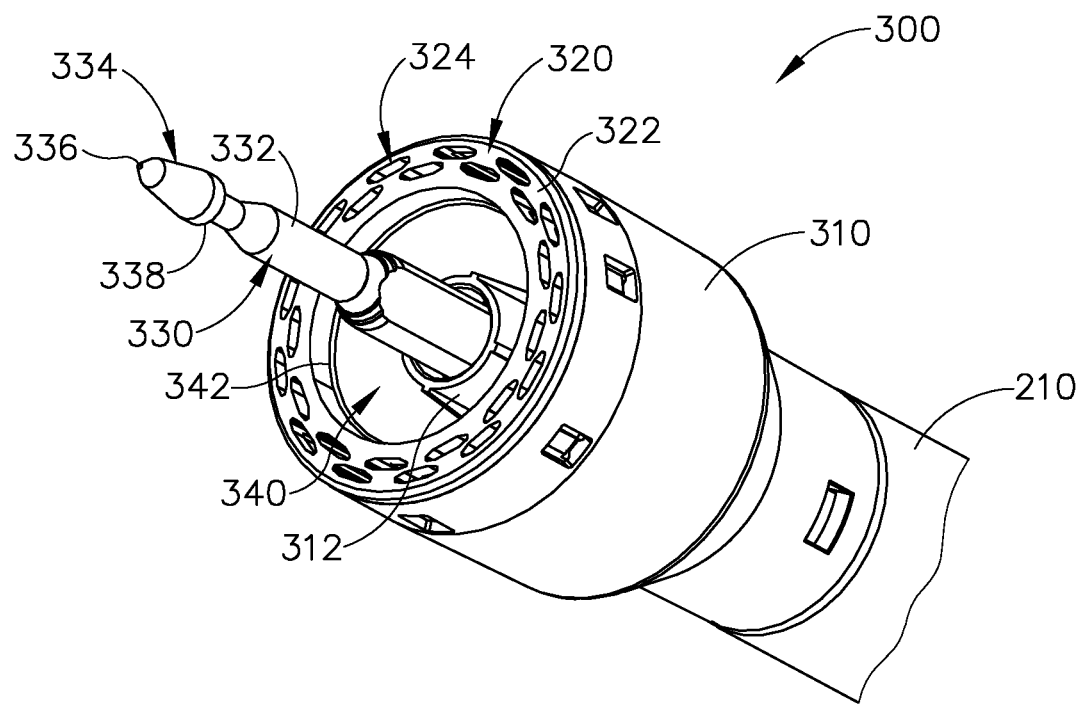
FIG. 4 depicts a perspective view of the stapling head assembly of the circular stapler of FIG. 1.
Figure 5:
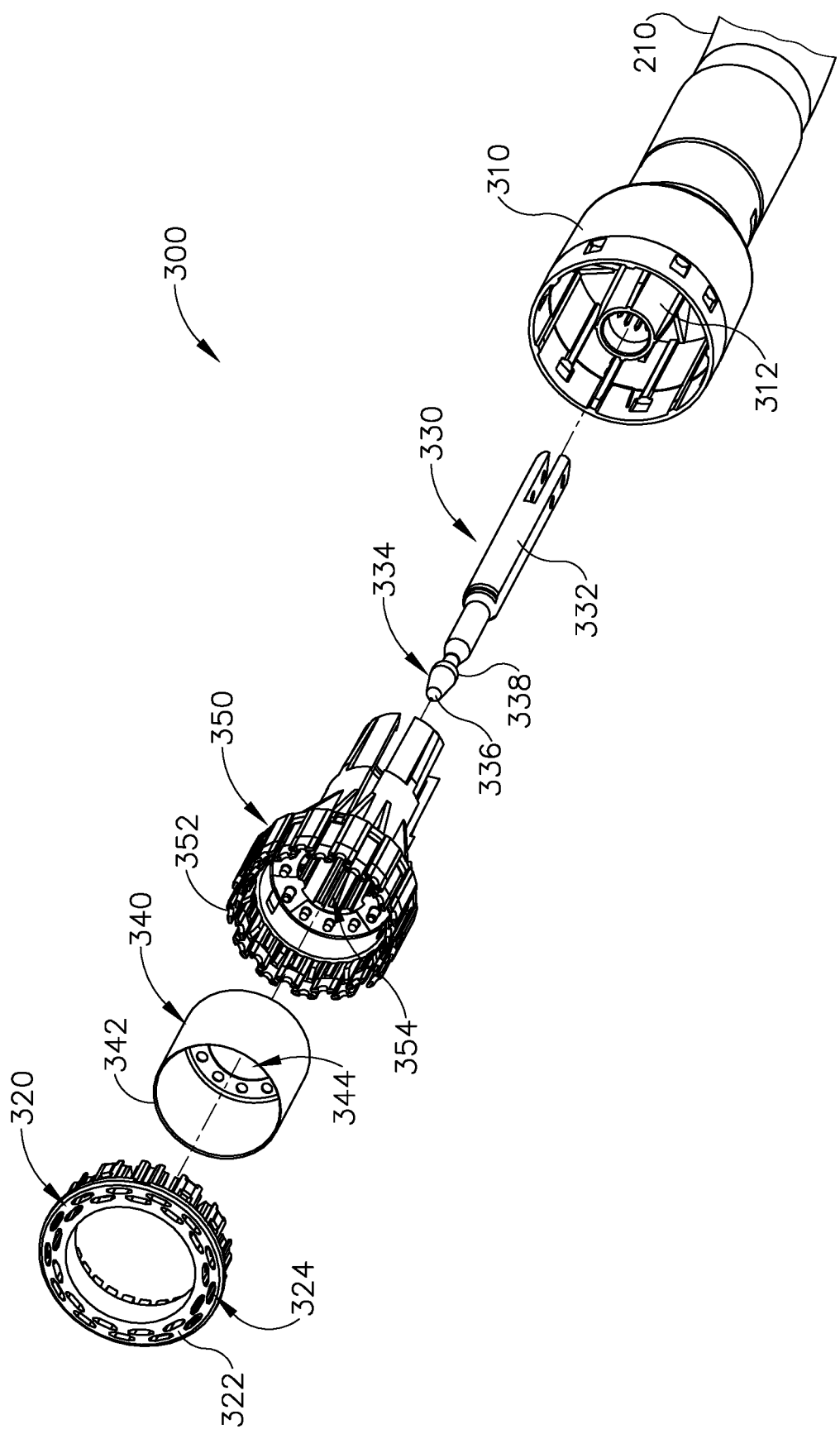
FIG. 5 depicts an exploded perspective view of the stapling head assembly of FIG. 4.

Stapling head assembly (300) is located at the distal end of shaft assembly (200). As shown in FIGS. 1-2, anvil (400) is configured to removably couple with shaft assembly (200), adjacent to stapling head assembly (300). As will be described in greater detail below, anvil (400) and stapling head assembly (300) are configured to cooperate to manipulate tissue in three ways, including clamping the tissue, cutting the tissue, and stapling the tissue. As best seen in FIGS. 4-5, stapling head assembly (300) of the present example comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). Trocar (330) is operable to translate distally and proximally relative to tubular casing (310) in response to rotation of a knob (130) located at the proximal end of handle assembly (100). Trocar (330) comprises a shaft (332) and a head (334). Head (334) includes a pointed tip (336) and an inwardly extending proximal surface (338). Head (334) and the distal portion of shaft (332) are configured for insertion in bore (422) of anvil (420). Proximal surface (338) is configured to complement features of latch members (430) to provide a snap fit between anvil (400) and trocar (330).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. Staple driver member (350) also defines a bore (354) that is configured to coaxially receive core member (312) of tubular casing (310).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310).

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. The arrangement of staple openings (322) may be modified just like the arrangement of staple forming pockets (414) as described above. It should also be understood that various structures and techniques may be used to contain staples within stapling head assembly (300) before stapling head assembly (300) is actuated. Deck member (320) defines an inner diameter that is just slightly larger than the outer diameter defined by knife member (340). Deck member (320) is thus configured to allow knife member (340) to translate distally to a point where cutting edge (342) is distal to deck surface (322). By way of example only, deck member (320) may be constructed and operable in accordance with at least some of the teachings of U.S. patent application Ser. No. 15/350,513, entitled "Circular Surgical Stapler with Recessed Deck," filed Nov. 14, 2016, published as U.S. Pub. No. 2018/0132853 on May 17, 2018, the disclosure of which is incorporated by reference herein. Other suitable configurations that may be used for deck member (320) will be apparent to those of ordinary skill in the art in view of the teachings herein.

Figure 6:
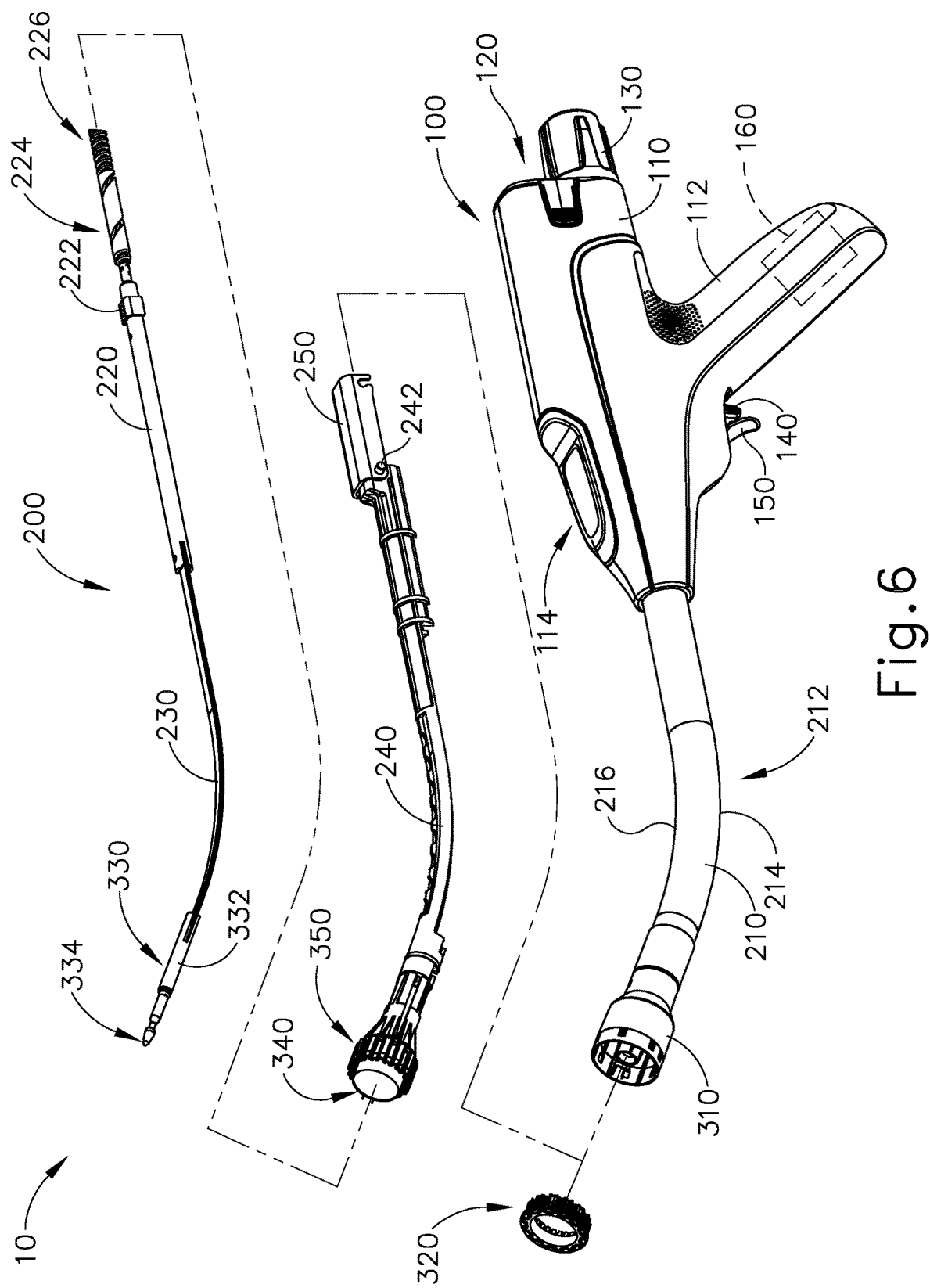
FIG. 6 depicts an exploded perspective view of the circular stapler of FIG. 1, with portions of the shaft assembly shown separately from each other.

FIG. 6 shows various components of shaft assembly (200), which extends distally from handle assembly (100) and couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section (212) that is configured to facilitate positioning of stapling head assembly (300) within a patient's colon as described below. Curved section (212) includes an inner curve (216) and an outer curve (214).

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220), such that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

Motor (160) is coupled with drive bracket (250) via a cam member (162) and a pivoting arm (164). Pivoting arm (164) is pivotably coupled with housing (166) of handle assembly (100) via a pin (116). Motor (160) is operable to rotate cam member (162). Cam member (162) is configured to drive pivotal movement of pivoting arm (164) when cam member (162) rotates in response to activation of motor. Pivoting arm (164) is configured to drive translation of drive bracket (250) when pivoting arm (164) pivots about pin (116) in response to rotation of cam member (162). Motor (160) is thus operable to drive stapling head assembly driver (240) via cam member (162), pivoting arm (164), and drive bracket (250). By way of example only, these components may be configured and operable in accordance with at least some of the teachings of U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 3, 2017, the disclosure of which is incorporated by reference herein.

Battery pack (120) is operable to provide electrical power to a motor (160) as noted above. Battery pack (120) may be removably coupled with handle assembly (100) through a snap fit or in any other suitable fashion. Battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) is unitarily incorporated within handle assembly (100) such that battery back (120) cannot be removed from handle assembly (100).

B. Exemplary User Input Features of Circular Stapling Instrument

Figure 7:
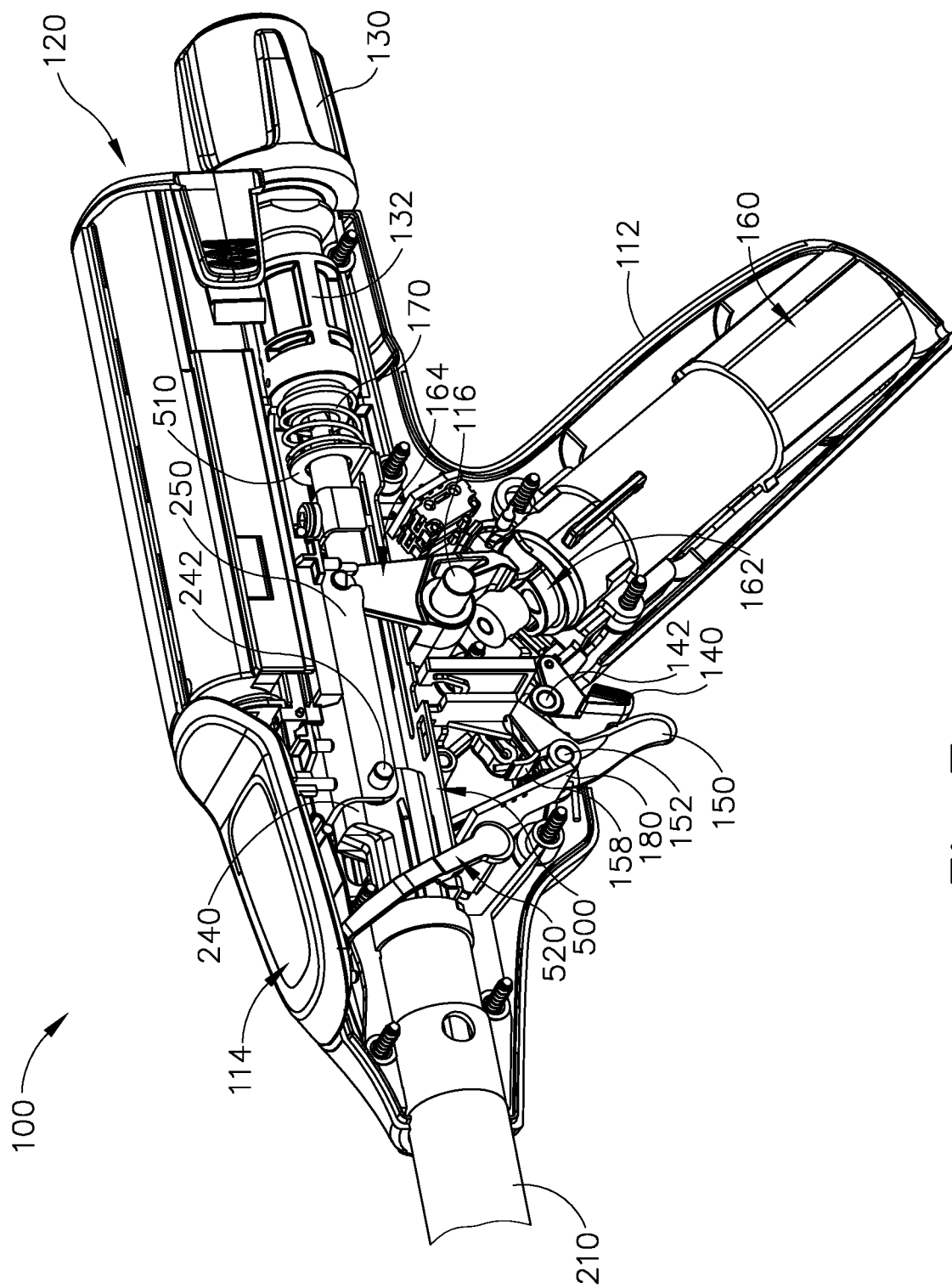
FIG. 7 depicts a perspective view of the handle assembly of the circular stapler of FIG. 1, with a housing half omitted to reveal internal components of the handle assembly.

As shown in FIGS. 1 and 7, handle assembly (100) includes a pistol grip (112) and several components that are operable to actuate anvil (400) and stapling head assembly (300). In particular, handle assembly (100) includes knob (130), a safety trigger (140) a firing trigger (150), a motor (160), and a motor activation module (180). Knob (130) is coupled with trocar actuation rod (220) via a nut (132), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130) in a first direction. Trocar actuation rod (220) will translate distally in response to rotation of knob (130) in a second direction.

Handle assembly (100) also includes components that are operable to selectively lock out triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range. The components of handle assembly (100) that provide the foregoing operability will be described in greater detail below.

1. Exemplary Anvil Actuation Assembly

Knob (130) protrudes proximally from casing (110) of handle assembly and is rotatable relative to casing (110). As shown in FIG. 7, a nut (132) is secured to the distal end of knob (130). In the present example, nut (132) is fixedly secured to the distal end of knob (130) such that nut (132) will rotate unitarily with knob (130). Nut (132) and knob (130) are configured to cooperate with trocar actuation rod (220) to thereby translate trocar actuation rod (220) longitudinally relative to casing (110) in response to rotation of nut (132) and knob (130) relative to casing (110). As noted above, trocar (330) will translate longitudinally relative to outer sheath (210) in response to translation of trocar actuation rod (220) relative to outer sheath (210) and casing (110).

The proximal portion of trocar actuation rod (220) is positioned within handle assembly (100) to engage nut (132) and knob (130). In particular, trocar actuation rod (220) is positioned within handle assembly (100) such that coarse helical threading (224) will selectively engage a thread engagement feature (not shown) within the interior of nut (132); and such that fine helical threading (226) will selectively engage a thread engagement feature (not shown) within the interior of knob (130). In some versions, the thread engagement feature of nut (132) comprises an inwardly directed tab; while the thread engagement feature of knob (130) comprises a helical threading. Other suitable forms that such thread engagement features may take will be apparent to those of ordinary skill in the art in view of the teachings herein.

In the present example, when nut (132) and knob (130) are rotated relative to casing (110), trocar actuation rod (220) travels proximally through a first range of longitudinal motion where coarse helical threading (224) is engaged with nut (132) to provide a relatively rapid rate of translation. Fine helical threading (226) is not engaged with knob (130) during this range of motion. When nut (132) and knob (130) are further rotated relative to casing (110) after trocar actuation rod (220) completes the first range of motion, trocar actuation rod (220) will continue to travel proximally through a second range of longitudinal motion where fine helical threading (226) is engaged with knob (130) to provide a relatively slow rate of translation. Thus, trocar actuation rod (220) will translate proximally through a sequence of rapid translation followed by slow translation, based on engagement between coarse helical threading (224) and nut (132) followed by engagement between fine helical threading (226) and knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance (d) between opposing surfaces (412, 322) of anvil (400) and stapling head assembly (300) until a suitable gap distance (d) has been achieved as shown in FIG. 21C and as described in greater detail below.

2. Exemplary Trigger Lockout Assembly

As noted above, knob may be used to adjust the gap distance (d) between opposing surfaces (412, 322) of anvil (400) and stapling head assembly (300). Setting an appropriate gap distance (d) before actuating stapling head assembly (300) may be critical to the success of an anastomosis. For instance, if the gap distance (d) is too great, the staples that are deployed at the anastomosis site may not be sufficiently formed by staple forming pockets (414). This may result in leakage at the anastomosis site, and in some cases may ultimately lead to the separation of the anatomical lumen sections that are joined at the anastomosis site. If the gap distance (d) is too small, the internal structure of the tissue compressed between surfaces (412, 322) may be damaged to the point where the structural integrity of the tissue is compromised. This may prevent the tissue from adequately holding the formed staples, which again may result in leakage or other failure of the anastomosis. It may therefore be desirable to provide the operator with some form of feedback indicating whether the gap distance (d) is within an appropriate range. It may also be desirable to prevent the operator from actuating stapling head assembly (300) unless the gap distance (d) is within an appropriate range.

Figure 8:
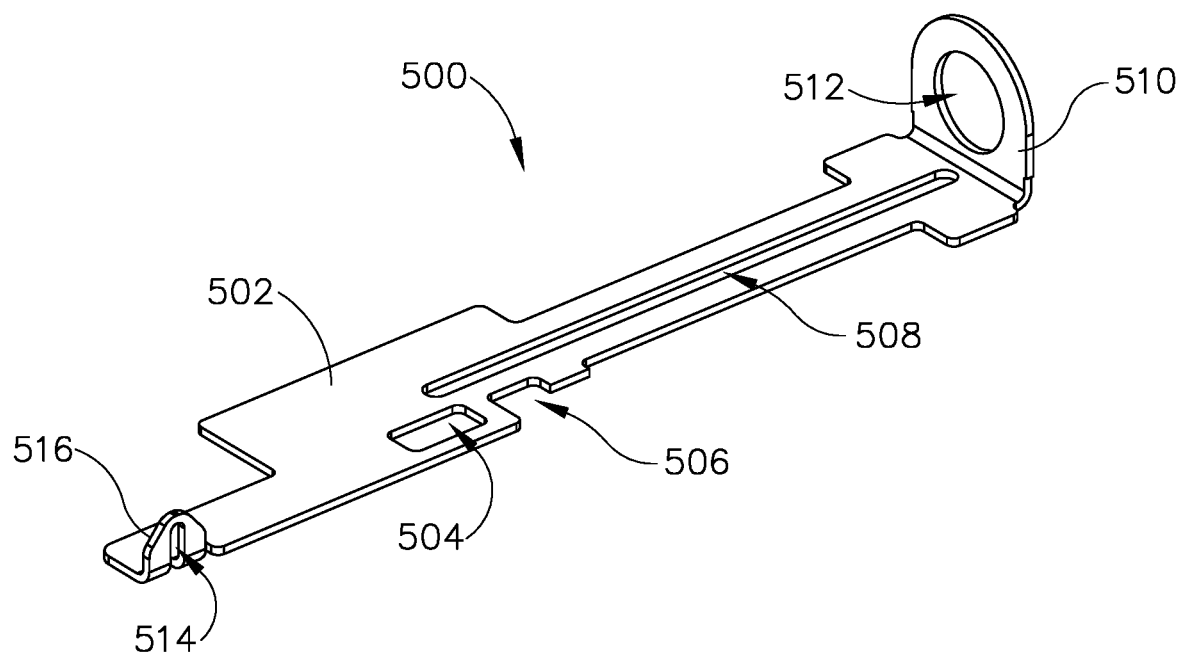
FIG. 8 depicts a perspective view of a bracket of the handle assembly of FIG. 7.

FIGS. 7-11 show components that provide feedback to the operator to indicate whether the gap distance (d) is within an appropriate range; and prevent the operator from actuating stapling head assembly (300) unless the gap distance (d) is within an appropriate range. As best seen in FIGS. 10B-10C, a bracket (500) is configured and positioned to move in response to movement of trocar actuation rod (220). As best seen in FIG. 8, bracket (500) includes a rigid body (502) that defines a first slot (504), a second slot (506), and a third slot (508). An upright feature (510) is positioned at the proximal end of body (502) and defines an opening (512). Trocar actuation rod (220) extends coaxially through opening (512). As shown in FIG. 7, a coil spring (170) is interposed between the proximal end of upright feature (510) and a rigid bulkhead feature that is defined by casing (110) and that forms a support journal for nut (132). The bulkhead is fixed within casing (110) and thereby provides a ground for the proximal end of coil spring (170), such that coil spring (170) resiliently imparts a distal bias to bracket (500) via upright feature (510). Bracket (500) further includes a laterally presented flange (516) at the distal end of body (502). Flange (516) defines a slot (514).

Figure 9:
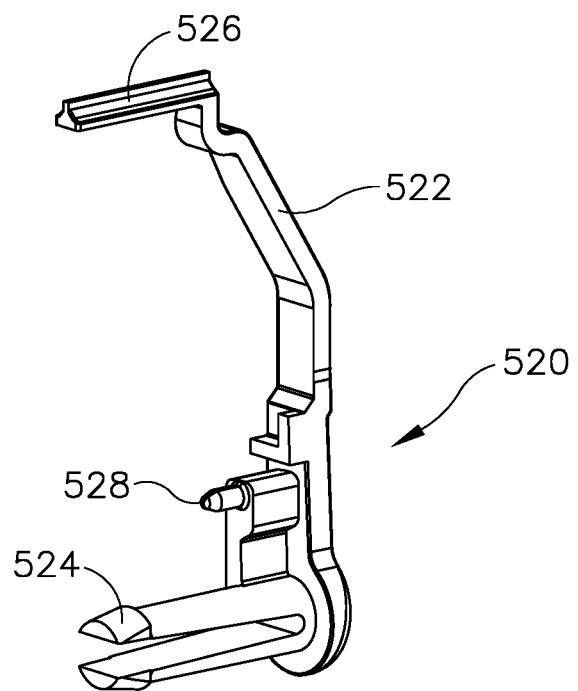
FIG. 9 depicts a perspective view of an indicator member of the handle assembly of FIG. 7.
Figure 10A:
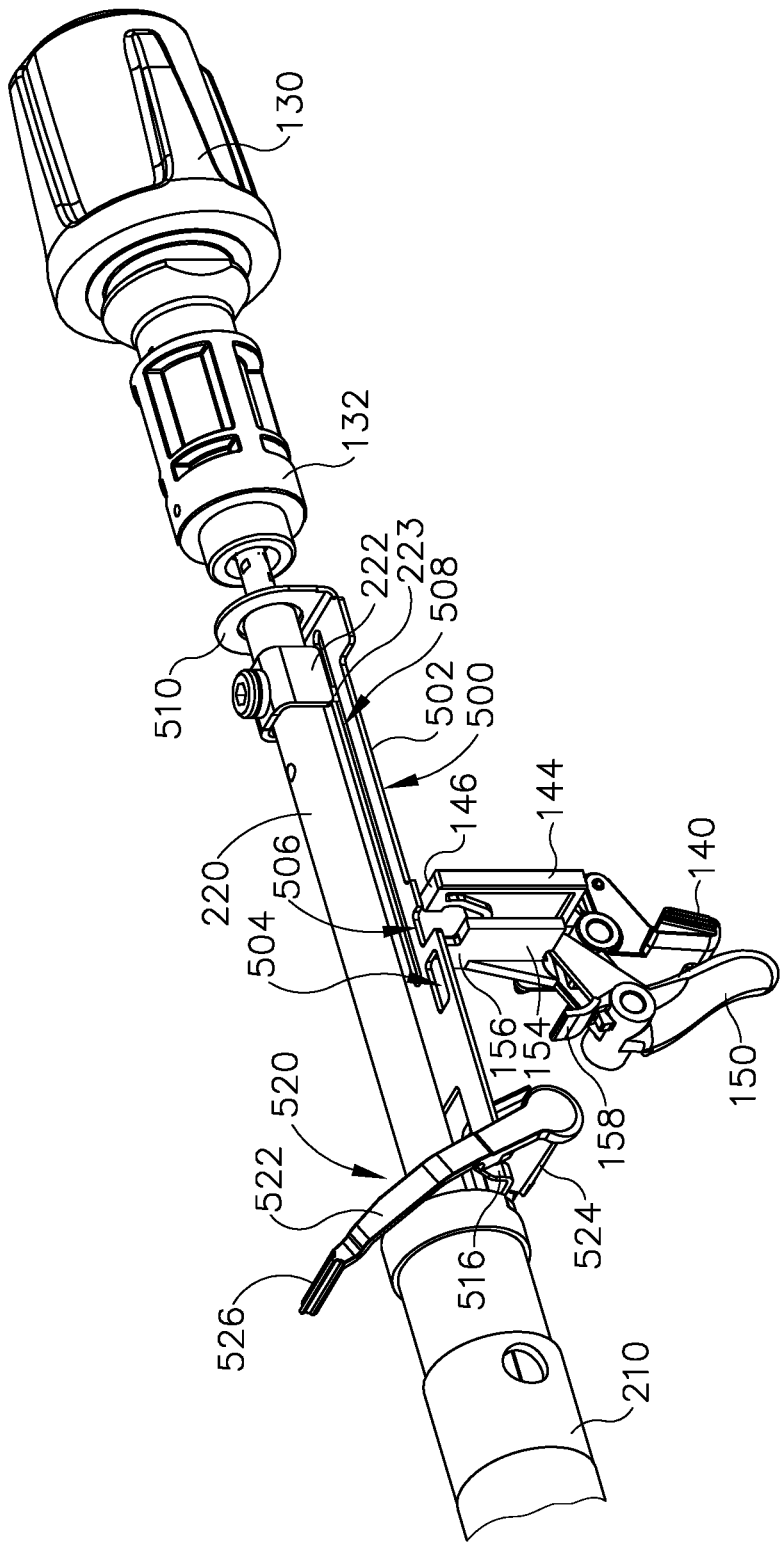
FIG. 10A depicts a perspective view of an anvil actuation assembly of the circular stapler of FIG. 1, an actuation rod in a first position.
Figure 10B:
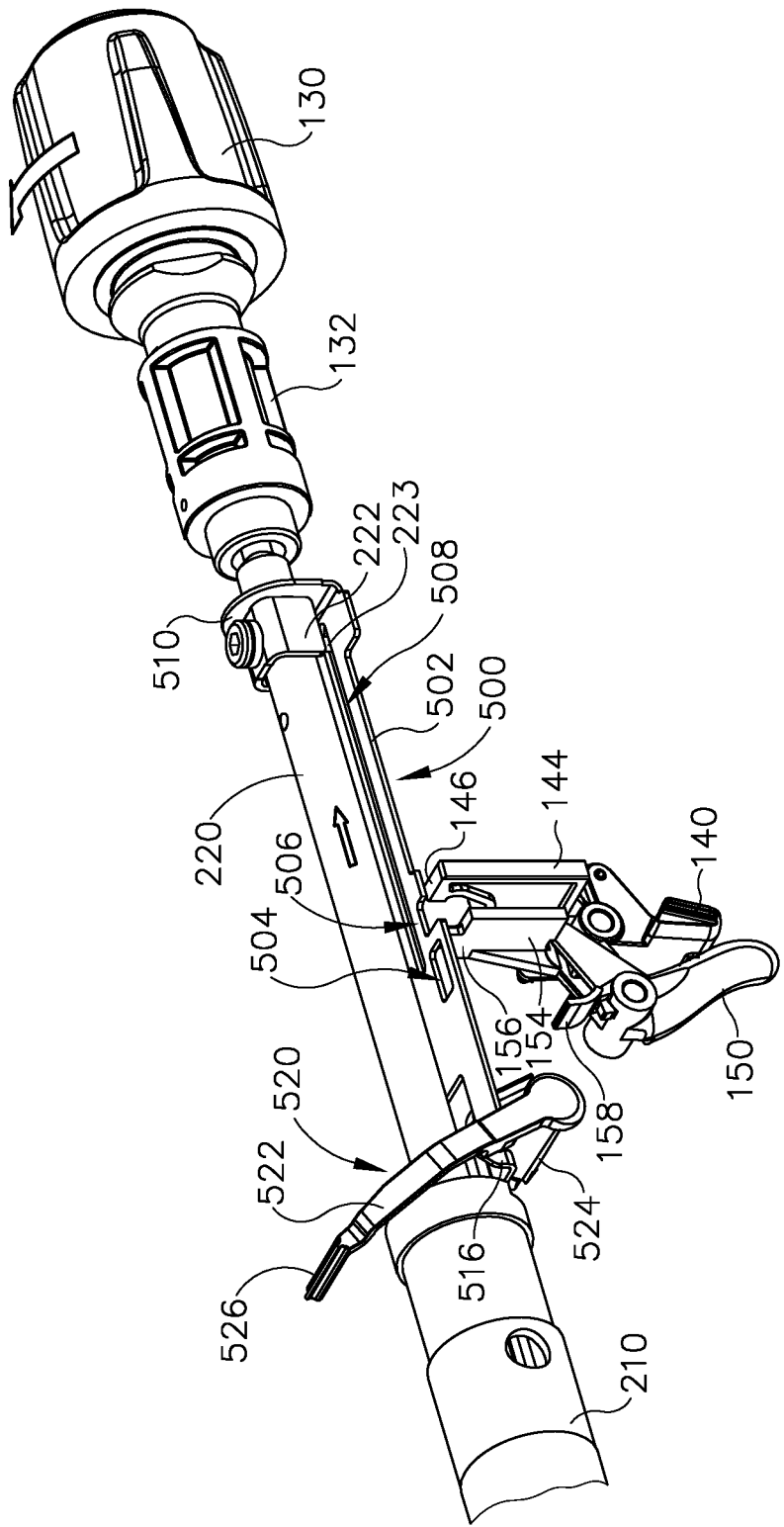
FIG. 10B depicts a perspective view of the anvil actuation assembly of FIG. 10A, with the actuation rod moved to a second position to engage the bracket of FIG. 8.
Figure 10C:
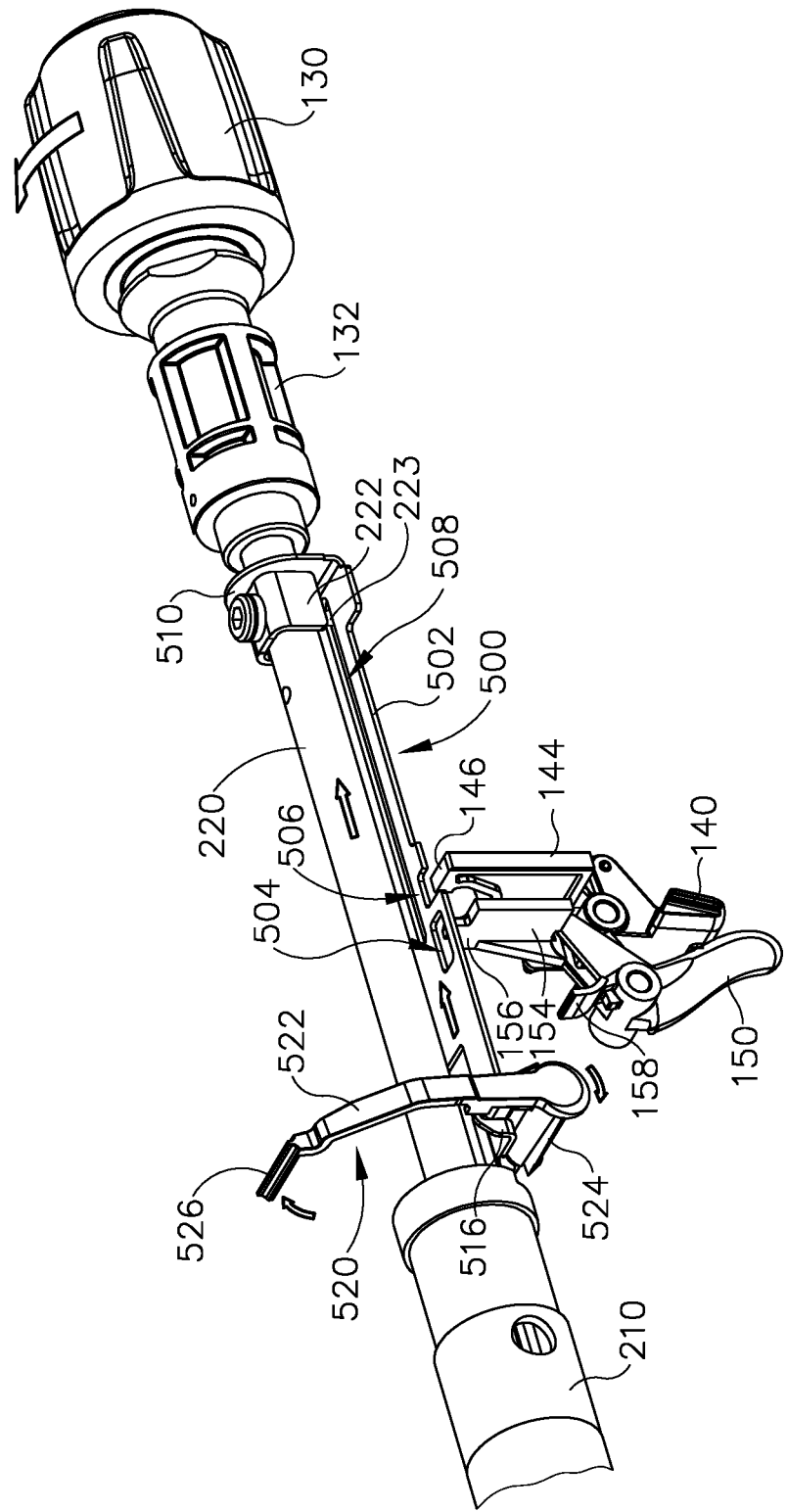
FIG. 10C depicts a perspective view of the anvil actuation assembly of FIG. 10A, with the actuation rod moved to a third position to retract the bracket of FIG. 8 proximally.

As best seen in FIGS. 10B-10C, an indicator member (520) is configured to pivot in response to translation of bracket (500). As best seen in FIG. 9, indicator member (520) comprises an upright arm (522), a snap pin (524) projecting laterally from a lower end of arm (522), an indicator needle (526) projecting laterally from an upper end of arm (522), and a coupling pin (528) projecting laterally from an intermediate region of arm (522). Snap pin (524) is configured to snap into a complementary recess provided by casing (110). Snap pin (524) thereby secures indicator member (520) to casing (110) yet permits indicator member (520) to pivot relative to casing (110) about the longitudinal axis of snap pin (524). Indicator needle (526) is positioned to be visible in a user feedback feature (114) of handle assembly (110) to thereby visually indicate the pivotal position of indicator member (520), as described in further detail below. Coupling pin (528) is slidably received in slot (514) of flange (516) of bracket (500). This engagement between indicator member (520), casing (110), and bracket (500) provides pivotal movement of indicator member (520) in response to translation of bracket (500).

Bracket (500) is configured to selectively prevent and permit actuation of triggers (140, 150). In particular, slots (504, 506) of bracket (500) are configured to selectively provide clearance for actuation of triggers (140, 150). As shown in FIGS. 10A-7E, safety trigger (140) is pivotably coupled with a first upright member (144). First upright member (144) is coupled with casing (110) such that first upright member (144) is configured to translate upwardly in response to pivoting of safety trigger (140) toward pistol grip (112). However, body (502) of bracket (500) is configured to prevent this movement of first upright member (144) and safety trigger (140) by engaging the upper end (146) of first upright member (144). Body (502) thus blocks movement of first upright member (144) and safety trigger (140) until bracket (500) is moved to a position where slot (506) is aligned with upper end (146) to thereby provide clearance for upward movement of first upright member (144). It should therefore be understood that safety trigger (140) cannot be pivoted toward pistol grip (112) until slot (506) is positioned over upper end (146).

Similarly, firing trigger (150) is pivotably coupled with a second upright member (154). Second upright member (154) is coupled with casing (110) such that second upright member (154) is configured to translate upwardly in response to pivoting of safety trigger (150) toward pistol grip (112). However, body (502) of bracket (500) is configured to prevent this movement of second upright member (154) and firing trigger (150) by engaging the upper end (156) of second upright member (154). Even if safety trigger (140) is pivoted out of the way to otherwise permit movement of firing trigger (150), body (502) blocks movement of second upright member (154) and firing trigger (150) until bracket (500) is moved to a position where slot (504) is aligned with upper end (156) to thereby provide clearance for upward movement of second upright member (154). It should therefore be understood that, even if safety trigger (140) is pivoted out of the way to otherwise permit movement of firing trigger (150), firing trigger (150) cannot be pivoted toward pistol grip (112) until slot (504) is positioned over upper end (156).

Third slot (508) is configured to receive a downwardly projecting boss (223) of clip (222), which is rigidly secured to trocar actuation rod (220). While casing (110) is configured to allow bracket (500) to translate longitudinally within casing (110), casing (110) includes rails, channels, and/or other features that prevent bracket (500) from rotating within casing (110). Thus, the positioning of boss (223) in slot (508) prevents clip (222) and trocar actuation rod (220) from rotating within casing (110). Boss (223) and slot (508) nevertheless allow bracket (500) to translate longitudinally within casing (110) as will be described in greater detail below.

FIGS. 10A-10E depict the above-described components at various stages of operation. In particular, in FIG. 10A, trocar actuation rod (220) is in a distal-most position, such that trocar (330) is in a distal-most position. At this stage, the operator may couple anvil (400) with trocar (330) by inserting trocar (330) into bore (422) until latch members (430) are secured to head (334) of trocar (330). The operator then rotates knob (130), which rotates nut (132). As knob (130) and nut (132) rotate, engagement between coarse helical threading (224) of trocar actuation rod (220) and the complementary feature of nut (132) causes trocar actuation rod (220) to retract proximally at a relatively rapid rate, such that trocar actuation rod (220) reaches the position shown in FIG. 10B. This provides proximal retraction of trocar actuation rod (220) provides retraction of trocar (330) and anvil (400). As trocar actuation rod (220) moves from the position shown in FIG. 10A to the position shown in FIG. 10B, bracket (500) remains stationary. This is due to the fact that clip (222) is spaced apart from upright feature (510) at the stage shown in FIG. 10A and does not engage upright feature (510) until trocar actuation rod (220) reaches the position shown in FIG. 10B.

After reaching the stage shown in FIG. 10B, the operator may continue rotating knob (130) and nut (132), which causes further proximal retraction of trocar actuation rod (220) as shown in FIG. 10C. This of course causes further proximal retraction of trocar (330) and anvil (400). As trocar actuation rod (220) moves from the position shown in FIG. 10B to the position shown in FIG. 10C, clip (222) bears against bracket (500), driving bracket (500) proximally. This proximal movement of bracket (500) causes indicator member (520) to pivot from the position shown in FIG. 10B to the position shown in FIG. 10C due to the positioning of pin (528) in slot (514) of flange (516).

Figure 11:
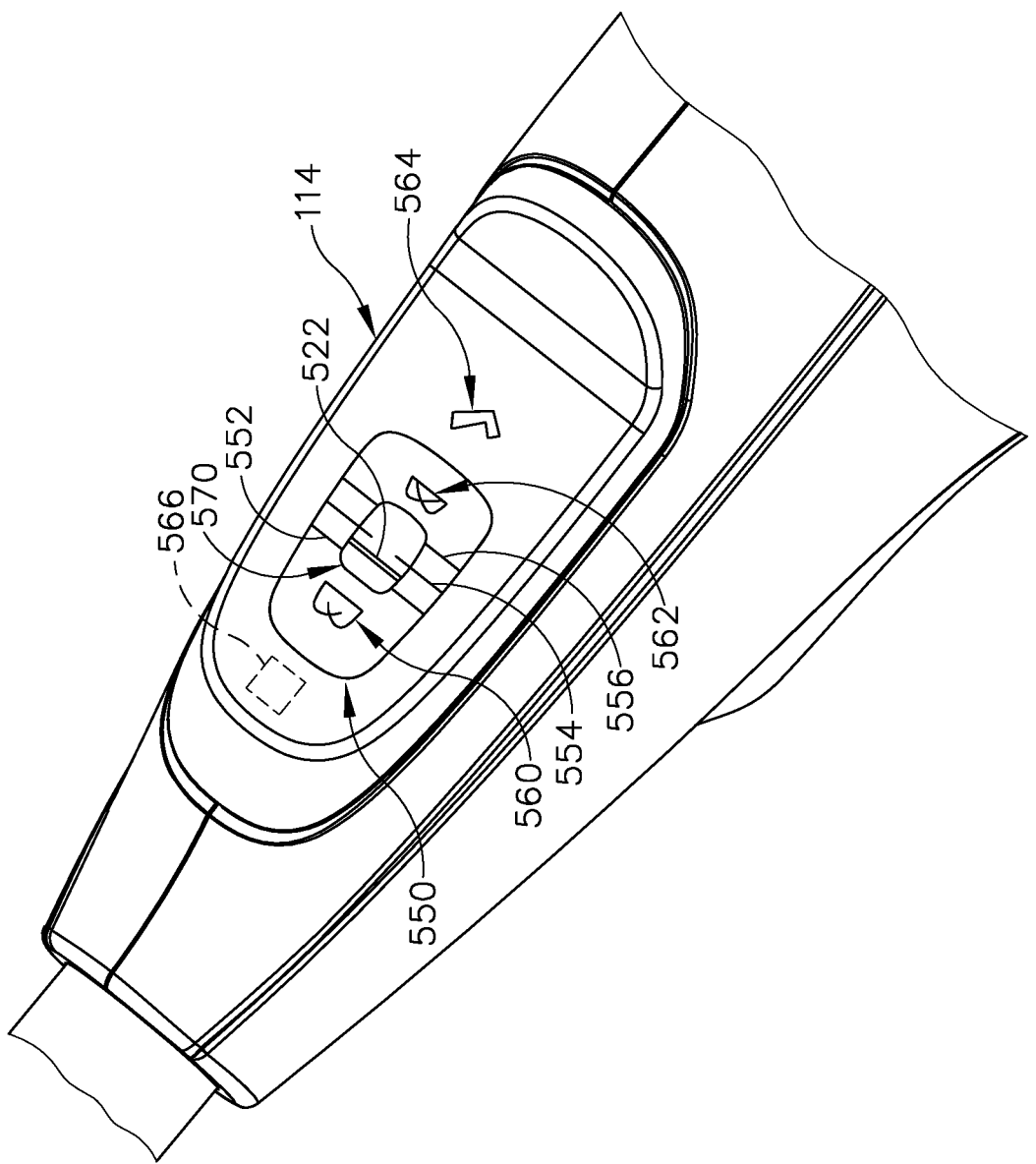
FIG. 11 depicts a perspective view of a user interface of the handle assembly of FIG. 7.

As indicator member (520) pivots from the position shown in FIG. 10B to the position shown in FIG. 10C, the operator may observe the position of indicator needle (526) in user feedback feature (114) of handle assembly (110). In particular, and as best seen in FIG. 11, user feedback feature (114) of the present example includes a graphical indicator (550), which includes fixed linear indicia (552, 554, 556), graphical representations (560, 562) of staples, and a checkmark graphic (564). User feedback feature (114) further defines a window (570) through which indicator needle (526) may be viewed. In some variations, user feedback feature (114) further includes a field (566) that may indicate the size of staples in stapling head assembly (300), the size of the gap defined between anvil (400) and stapling head assembly (300), and/or other information.

As the operator rotates knob (130) to adjust the longitudinal position of anvil (400) relative to stapling head assembly (300), the operator may observe the position of indicator needle (526) through window (570). Initially, indicator needle (526) may be positioned at or near the distal end of window (570). As anvil (400) continues to move proximally, indicator needle (526) will eventually move proximally relative to window (570). The operator may view the position of indicator needle (526) in relation to fixed linear indicia (552, 554, 556). The distal-most and proximal-most indicia (552, 556) may represent the boundaries of a "green zone," which is the acceptable range of distance between anvil (400) and stapling head assembly (300) for successful actuation of stapling head assembly (300). Thus, if indicator needle (526) is distal to distal-most indicia (552), the distance between anvil (400) and stapling head assembly (300) is too large; and if indicator needle (526) is proximal to proximal-most indicia (556), the distance between anvil (400) and stapling head assembly (300) is too small. Indicia (554) is longitudinally positioned between indicia (552, 556). Graphical representation (560) represents a relatively tall formed staple (e.g., suitable for use in relatively thick tissue); while graphical representation (562) represents a relatively short formed staple (e.g., suitable for use in relatively thin tissue). Graphical representations (560, 562) may thus facilitate the operator's decision, based on tissue observations or otherwise, on whether and how to achieve a desired formed staple height by selecting an appropriate corresponding spatial relationship between indicator needle (526) and indicia (552, 554, 556).

In the present example, window (570) is illuminated via a light emitting diode (LED) (not shown), further facilitating viewing of indicator needle (526) in window (570). In addition, checkmark graphic (564) is illuminated via another LED (not shown) when stapling head assembly (300) completes a stapling and cutting cycle. Thus, the operator may further rely on illumination of checkmark graphic (564) to verify that it is safe to advance anvil (400) distally away from the anastomosis (70) and remove instrument (10) from the patient. By way of example only, the LED associated with window (570) may be configured to emit white visible light while the LED associated with checkmark graphic (564) may be configured to emit green visible light.

In order to provide fine control of the gap distance (d) adjustment at the stage shown in FIG. 10C, trocar actuation rod (220) will be at a longitudinal position where fine helical threading (226) is engaged with a complementary feature of knob (130) and coarse helical threading (224) is disengaged from the complementary feature of nut (132). In some versions, coarse helical threading (224) disengages nut (132) and fine helical threading (226) begins to engage knob (130) once trocar actuation rod (220) reaches the longitudinal position shown in FIG. 10B (i.e., when clip (222) first engages upright member (510)). In some other versions, the transition from engagement by coarse helical threading (224) to fine helical threading (226) occurs sometime between the stage shown in FIG. 10B and the stage shown in FIG. 10C. Other suitable stages at which the coarse-to-fine transition may occur will be apparent to those of ordinary skill in the art in view of the teachings herein. It should also be understood that some alternative versions of trocar actuation rod (220) may have just a single threading section, with the pitch of the threading being consistent along the length of the threading. In other words, trocar actuation rod (220) does not necessarily need to have two different sections of threading (224, 226) with different pitches.

At the stage shown in FIG. 10C, slot (506) is aligned with upper end (146) to thereby provide clearance for upward movement of first upright member (144). Similarly, slot (504) is aligned with upper end (156) to thereby provide clearance for upward movement of second upright member (154). In the present example, slots (504, 506) are sized and positioned such that slots (504, 506) only provide clearance for upward movement of upright members (144, 154) when the gap distance (d) is within a clinically acceptable range. By way of example only, a "clinically acceptable range" for the gap distance (d) may be between approximately 0.110 inches and approximately 0.040 inches. As another merely illustrative example, a "clinically acceptable range" for the gap distance (d) may be between approximately 0.110 inches and approximately 0.020 inches. Even when slots (504, 506) are positioned to provide clearance for upward movement of upright members (144, 154) as shown in FIG. 10C, safety trigger (140) will still block pivotal movement of firing trigger (150) about a pin (152) (FIG. 7) when safety trigger (140) is in the non-actuated position shown in FIG. 10C. Thus, in order to enable movement of firing trigger (150), the operator will need to first actuate safety trigger (140) about a pin (142) (FIG. 7) from the position shown in FIG. 10C to the position shown in FIG. 10D.

Figure 10D:
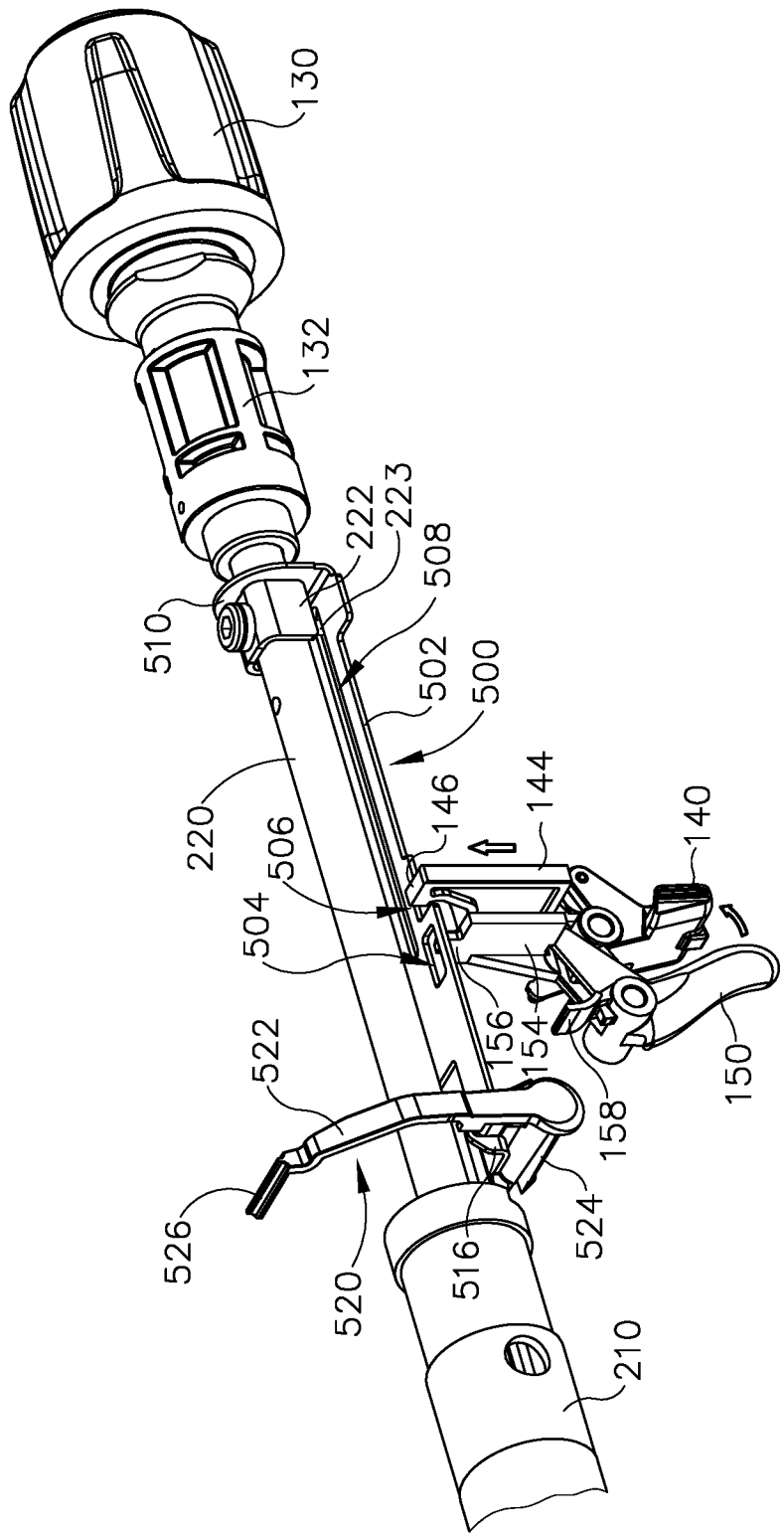
FIG. 10D depicts a perspective view of the anvil actuation assembly of FIG. 10A, with a safety trigger pivoted from a first position to a second position.

As shown in FIG. 10D, upper end (146) passes through slot (506) as safety trigger (140) is pivoted from the position shown in FIG. 10C to the position shown in FIG. 10D. It should be understood that this movement of upper end (146) would not be possible at the stages shown in FIGS. 10A-7B (when the gap distance (d) is too great) because body (502) would physically block upward movement of upright member (144), thereby physically blocking pivotal movement of safety trigger (140). In the present example, a cap (not shown) incorporated into knob (130) prevents knob (130) from rotating to a point where anvil (400) would be retracted too far proximally (such that the gap distance (d) is too small). In some other variations, even if knob (130) were to permit anvil (400) to be retracted too far proximally (such that the gap distance (d) is too small), body (502) would physically block upward movement of upright member (144), thereby physically blocking pivotal movement of safety trigger (140), in the event that the operator retracts trocar (330) and anvil (400) too far proximally (such that the gap distance (d) is too small). Regardless of whether body (502), knob (130), or some other feature prevents actuation when the gap distance (d) would be too small, it should be understood that instrument (10) permits actuation of safety trigger (140) only when the gap distance (d) is within the clinically acceptable range.

Figure 10E:
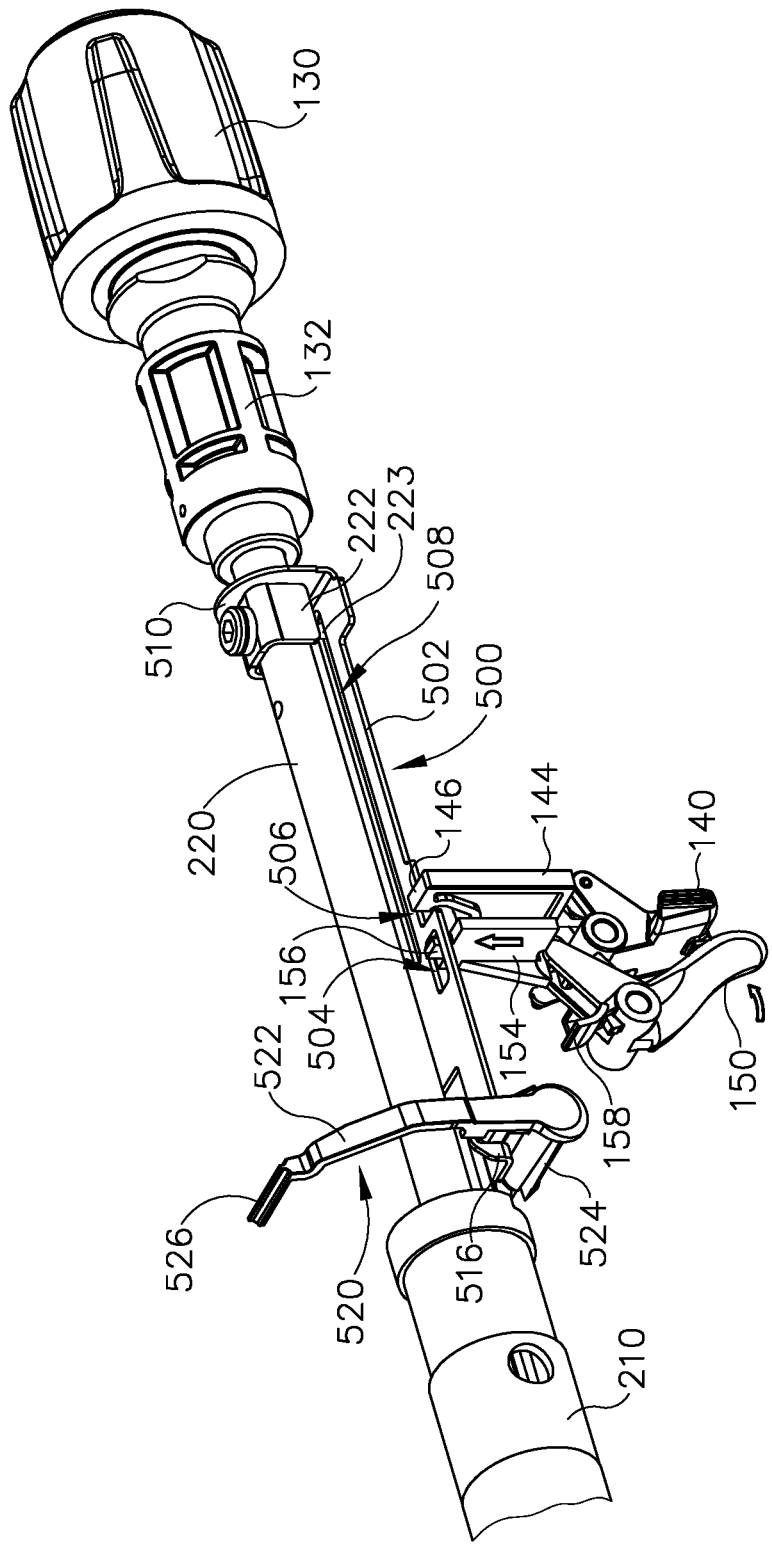
FIG. 10E depicts a perspective view of the anvil actuation assembly of FIG. 10A, with a firing trigger pivoted from a first position to a second position.

As noted above, safety trigger (140) is configured to prevent actuation of firing trigger (150) until safety trigger (140) has been actuated. Once safety trigger (140) has been actuated, the operator may actuate firing trigger (150) from the position shown in FIG. 10D to the position shown in FIG. 10E. As shown in FIG. 10E, upper end (156) passes through slot (504) as firing trigger (150) is pivoted from the position shown in FIG. 10D to the position shown in FIG. 10E. It should be understood that, even in the complete absence of safety trigger (140), this movement of upper end (156) would not be possible at the stages shown in FIGS. 10A-7B (when the gap distance (d) is too great) because body (502) would physically block upward movement of upright member (154), thereby physically blocking pivotal movement of firing trigger (150). It should also be understood that body (502) would also physically block upward movement of upright member (154), thereby physically blocking pivotal movement of firing trigger (150), in the event that the operator retracts trocar (330) and anvil (400) too far proximally (such that the gap distance (d) is too small). Thus, even in the complete absence of safety trigger (140), firing trigger (150) may only be actuated when the gap distance (d) is within the clinically acceptable range.

Firing trigger (150) of the present example includes an integral actuation paddle (158). Paddle (158) pivots forwardly as firing trigger (150) pivots from the position shown in FIG. 10D to the position shown in FIG. 10E. Paddle (158) is configured to actuate a switch of a motor activation module (180), which is shown in FIG. 7, when firing trigger (150) pivots from the position shown in FIG. 10D to the position shown in FIG. 10E. Motor activation module (180) is in communication with battery pack (120) and motor (160), such that motor activation module (180) is configured to provide activation of motor (160) with electrical power from battery pack (120) in response to paddle (158) actuating the switch of motor activation module (180). Thus, motor (160) will be activated when firing trigger (150) is pivoted from the position shown in FIG. 10D to the position shown in FIG. 10E. This activation of motor (160) will actuate stapling head assembly (300) as described in greater detail below.

C. Exemplary Anastomosis Procedure with Circular Stapling Instrument

FIGS. 12A-12E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. In some versions, one or more diseased portions of a patient's colon are removed, with the tubular anatomical structures (20, 40) of FIGS. 12A-12E representing the remaining severed portions of the colon.

Figure 12A:
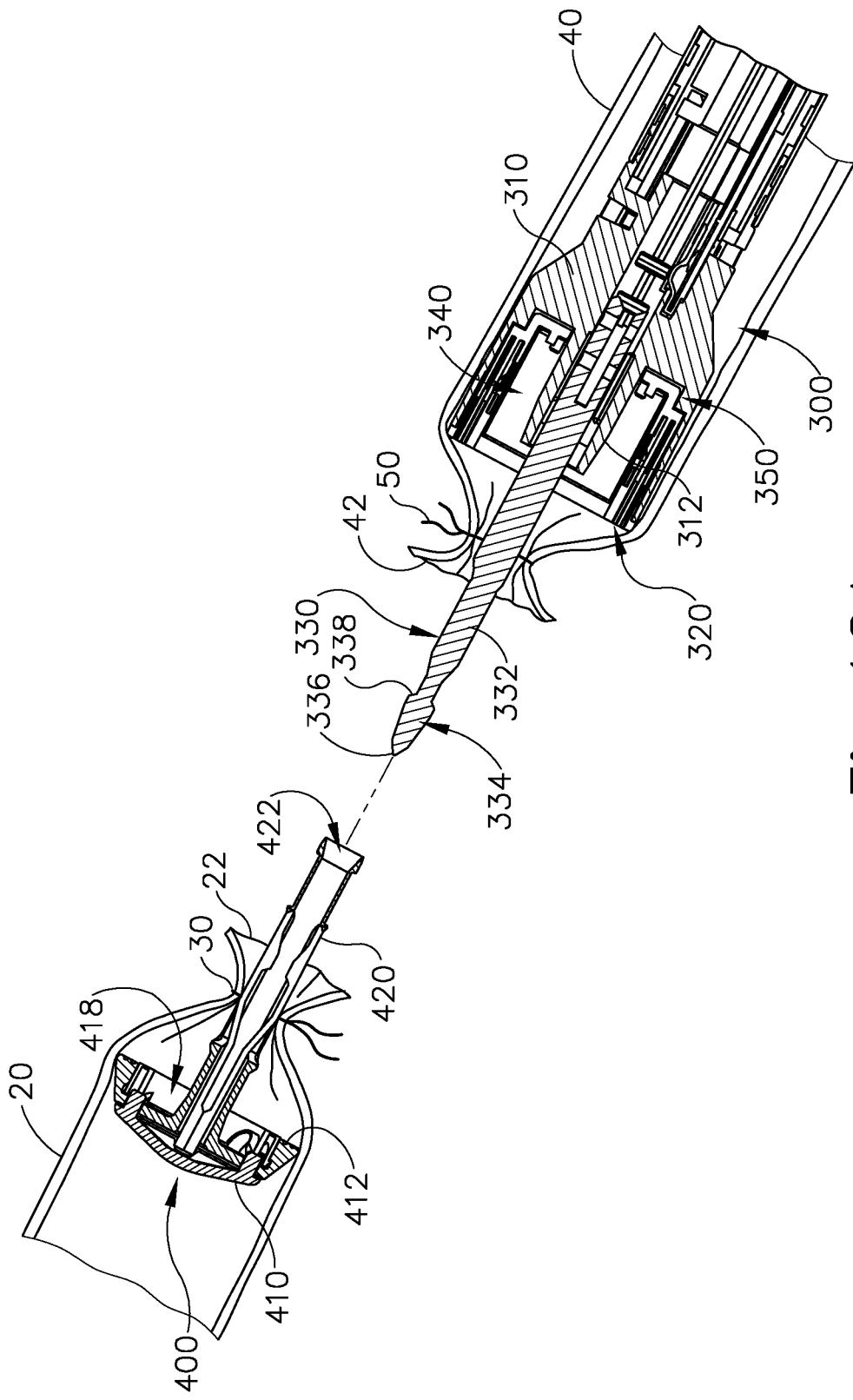
FIG. 12A depicts a cross-sectional side view of the anvil of FIG. 3 positioned within a first section of a digestive tract and the stapling head assembly of FIG. 4 positioned in a second section of the digestive tract, with the anvil separated from the stapling head assembly.

As shown in FIG. 12A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 12A-12E is an open surgical procedure, though the procedure may instead be performed laparoscopically. By way of example only, the surgical procedure may be performed laparoscopically in accordance with at least some of the teachings of U.S. Pub. No. 2016/0100837, entitled "Surgical Stapling Apparatus Comprising a Tissue Stop," published Apr. 14, 2016, the disclosure of which is incorporated by reference herein, issued as U.S. Pat. No. 10,076,325 on Sep. 18, 2018; and/or U.S. Pub. No. 2017/0086848, entitled "Apparatus and Method for Forming a Staple Line with Trocar Passageway," published Mar. 30, 2017, issued as U.S. Pat. No. 10,485,548 on Nov. 26, 2019, the disclosure of which is incorporated by reference herein. Various other suitable ways in which instrument (10) may be used to form an anastomosis (70) in a laparoscopic procedure will be apparent to those of ordinary skill in the art in view of the teachings herein.

As shown in FIG. 12A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Figure 12B:
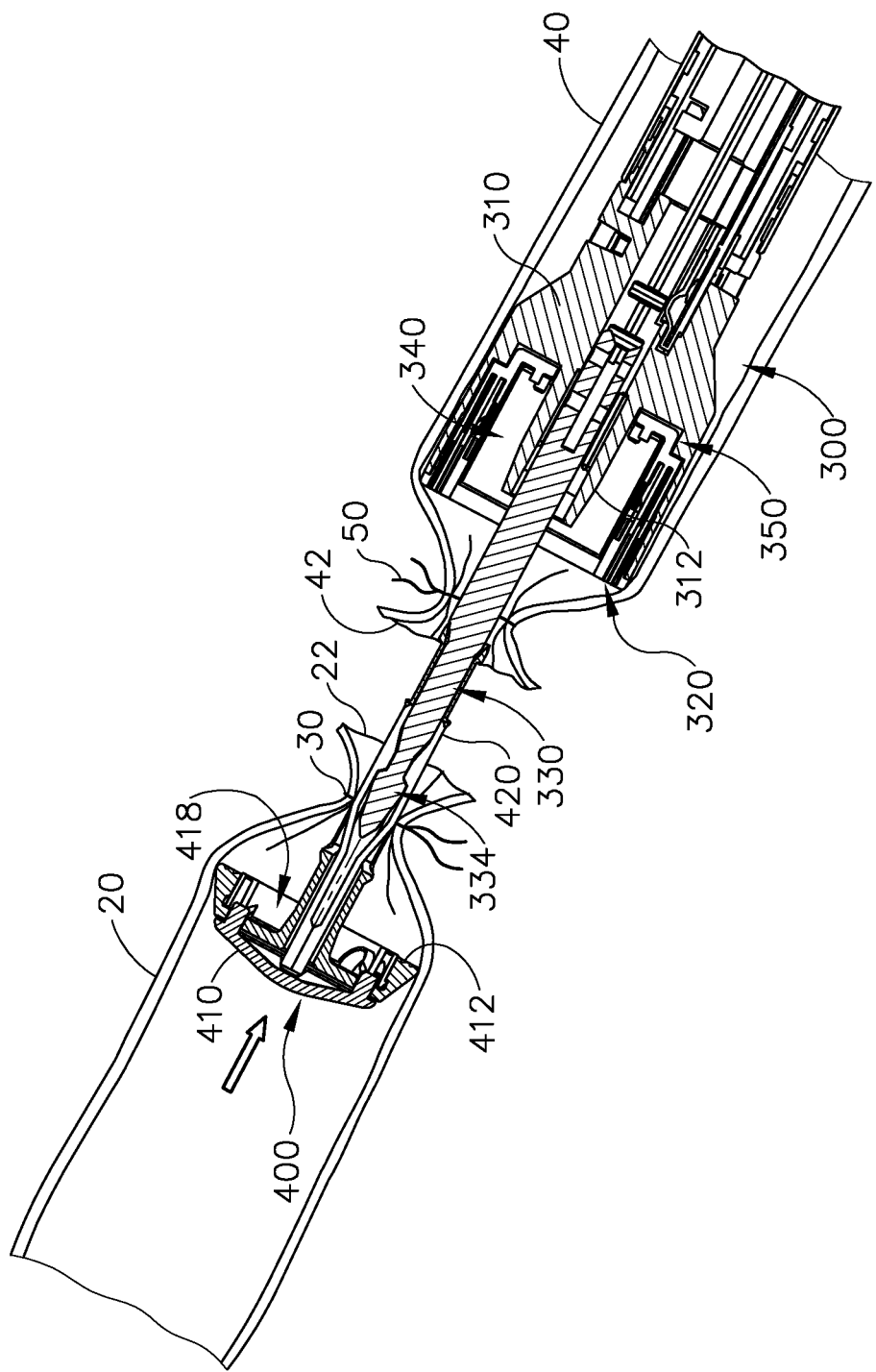
FIG. 12B depicts a cross-sectional side view of the anvil of FIG. 3 positioned within the first section of the digestive tract and the stapling head assembly of FIG. 4 positioned in the second section of the digestive tract, with the anvil secured to the stapling head assembly.
Figure 12C:
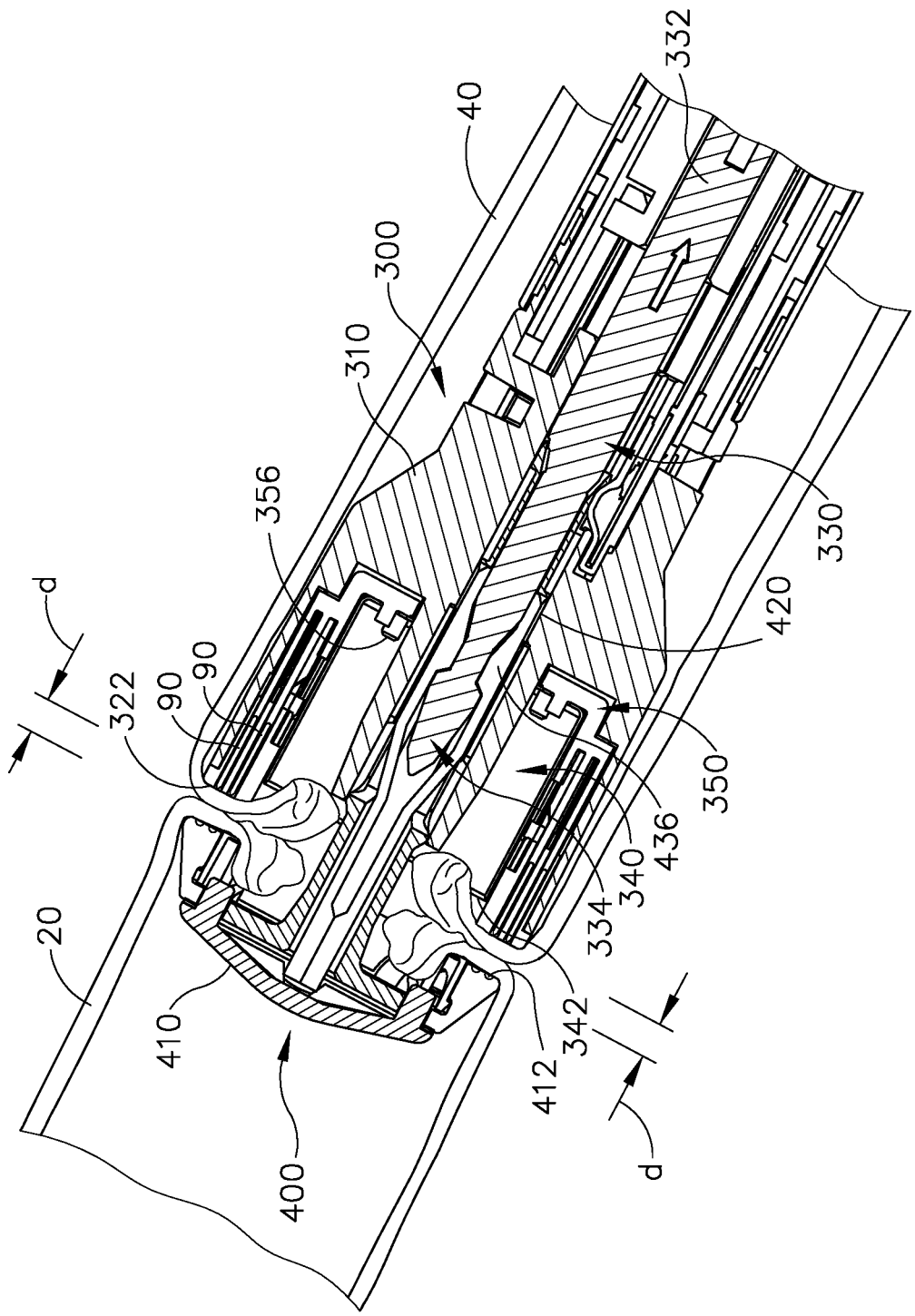
FIG. 12C depicts a cross-sectional side view of the anvil of FIG. 3 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 12B. Latch members (430) engage head (334) of trocar (330), thereby providing a secure fit between anvil (400) and trocar (330). The operator then rotates knob (130) while holding handle assembly (100) stationary via pistol grip (112). This rotation of knob (130) causes trocar (330) and anvil (400) to retract proximally, as described above. As shown in FIG. 12C, this proximal retraction of trocar (330) and anvil (400) compresses the tissue of tubular anatomical structures (20, 40) between surfaces (412, 322) of anvil (400) and stapling head assembly (300). The operator observes user feedback feature (114) to determine whether the gap distance (d) between opposing surfaces (412, 322) of anvil (400) and stapling head assembly (300) is appropriate; and makes any necessary adjustments via knob (130).

Figure 12D:
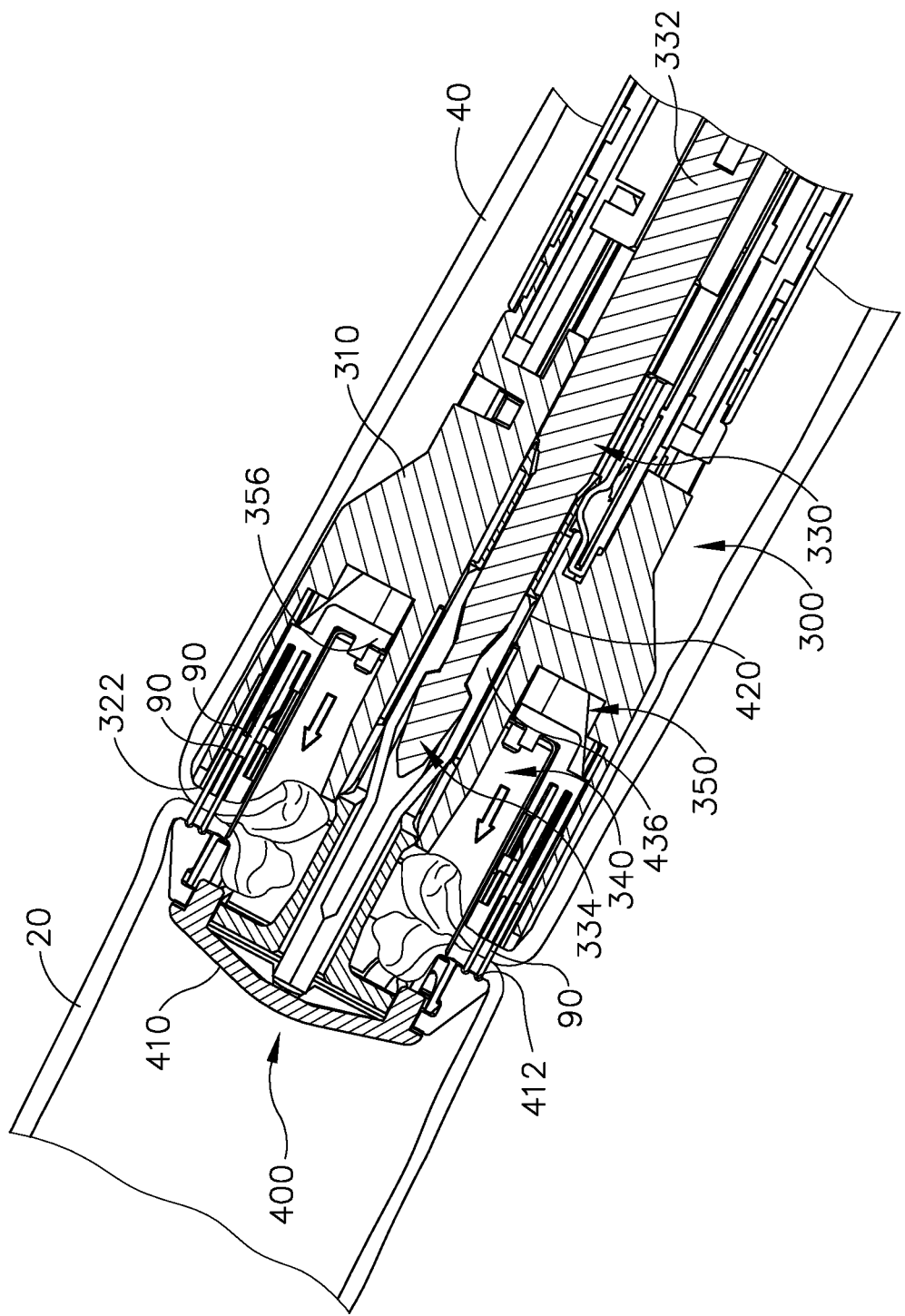
FIG. 12D depicts a cross-sectional side view of the anvil of FIG. 3 positioned within the first section of the digestive tract and the stapling head assembly of FIG. 4 positioned in the second section of the digestive tract, with the stapling head assembly actuated to sever and staple the clamped tissue.

Once the operator has appropriately set the gap distance (d) via knob (130), the operator actuates safety trigger (140) to enable actuation of firing trigger (150). The operator then actuates firing trigger (150). This actuation of firing trigger (150) in turn actuates a switch of motor activation module (180), which in turn activates motor (160) to thereby actuate stapling head assembly (300) by driving knife member (340) and staple driver member (350) distally as shown in FIG. 12D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 3, anvil (400) of the present example includes a breakable washer (417) within annular recess (418). This washer (417) is broken by knife member (340) when knife member (340) completes a full distal range of motion from the position shown in FIG. 12C to the position shown in FIG. 12D. The drive mechanism for knife member (340) may provide an increasing mechanical advantage as knife member (340) reaches the end of its distal movement, thereby providing greater force by which to break washer (417). Of course, breakable washer (417) may be omitted entirely in some versions. In versions where washer (417) is included, washer (417) may also serve as a cutting board for knife member (340) to assist in cutting of tissue. Such a cutting technique may be employed in addition to or in lieu of the above-noted shearing action between inner edge (416) and cutting edge (342).

As staple driver member (350) translates distally from the position shown in FIG. 12C to the position shown in FIG.

12D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together, thereby coupling tubular anatomical structure (20) with tubular anatomical structure (40).

Figure 12E:
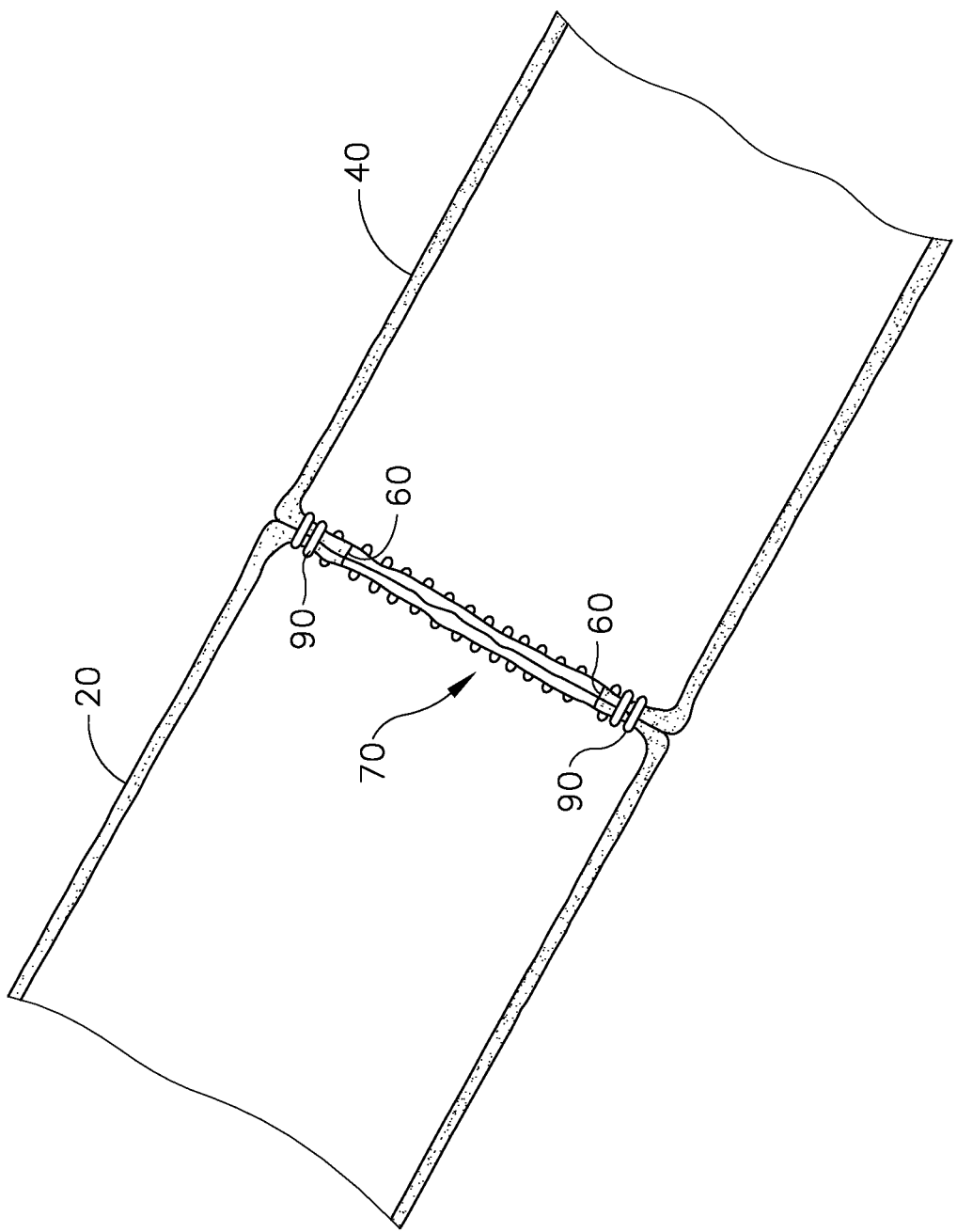
FIG. 12E depicts a cross-sectional side view of the first and second sections of the digestive tract of FIG. 12A joined together at an end-to-end anastomosis.

After the operator has actuated stapling head assembly (300) as shown in FIG. 12D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) removed, the tubular anatomical structures (20, 40) are left secured together by two annular arrays of staples (90) at an anastomosis (70) as shown in FIG. 12E. The inner diameter of the anastomosis (70) is defined by the severed edge (60) left by knife member (340).

II. Exemplary Alternative Trocar and Anvil Position Indicator Features

As noted above, indicator member (520) and user feedback feature (114) cooperate to provide the operator with visual feedback indicating the longitudinal position of anvil (400) relative to stapling head assembly (300). Those of ordinary skill in the art will recognize that the precision and in this positioning may be critical to the successful formation of an anastomosis (70). Thus, the real-time accuracy of the feedback provided by indicator member (520) and user feedback feature (114) may be critical to the successful formation of an anastomosis (70).

Some versions of bracket (500) and indicator member (520) may provide some degree of hysteresis, such that there is a slight lag time between the adjustment of the longitudinal position of anvil (400) relative to stapling head assembly (300) and the position of indicator member (520) in user feedback feature (114). This hysteresis may be attributable to manufacturing tolerances and/or other factors. This hysteresis may compromise the real-time accuracy of the feedback provided by indicator member (520) and user feedback feature (114), which may in turn compromise the success of the anastomosis (70). It may therefore be desirable to configure bracket (500), indicator member (520), and associated features to eliminate or at least minimize such hysteresis, to thereby promote greater real-time accuracy of the feedback provided by indicator member (520) and user feedback feature (114), to in turn thereby promote a greater chance of success in the formation of an anastomosis (70).

Figure 13:
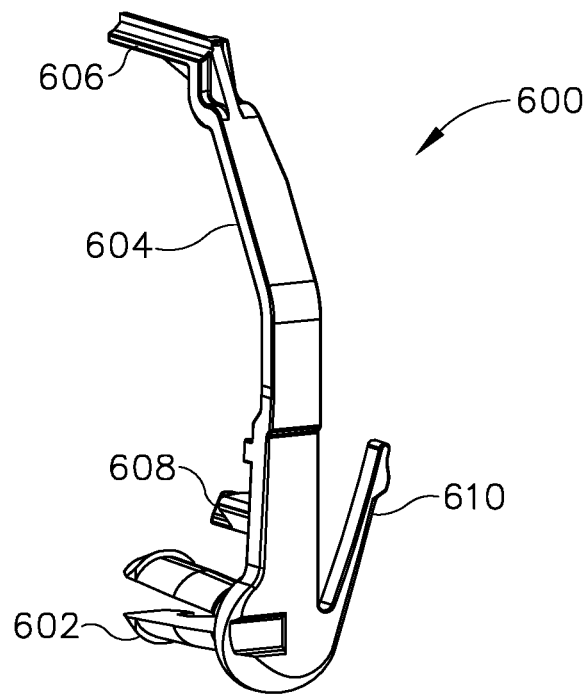
FIG. 13 depicts a perspective view of an exemplary alternative indicator member that may be incorporated into the instrument of FIG. 1.
Figure 14:
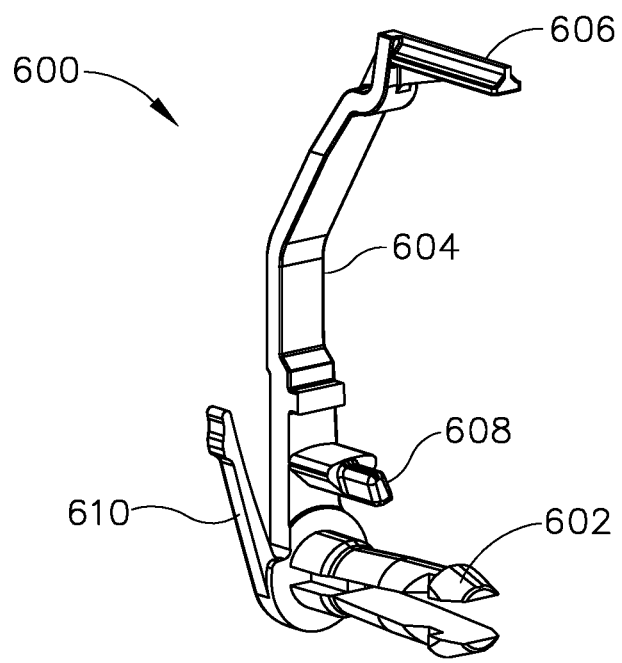
FIG. 14 depicts another perspective view of the indicator member of FIG. 13.
Figure 15:
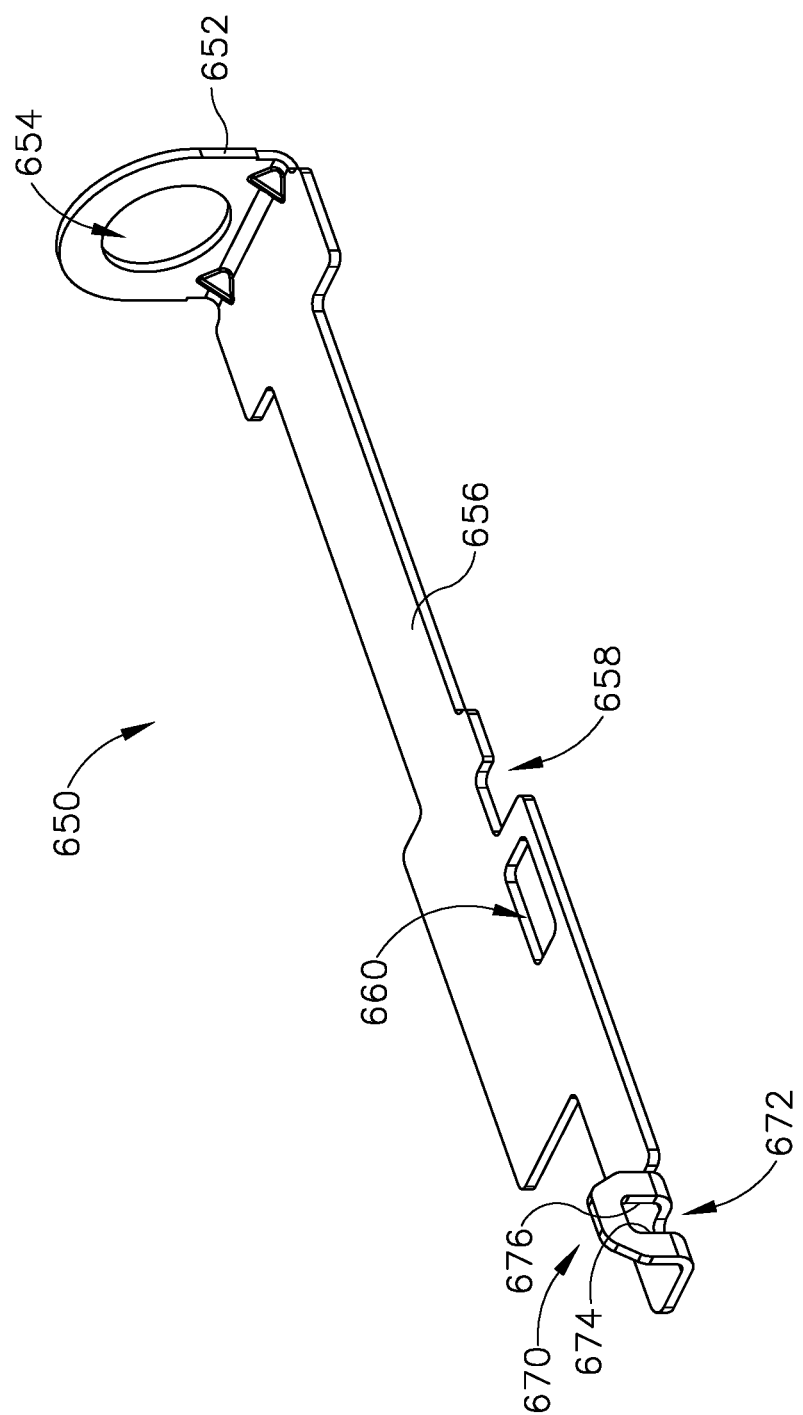
FIG. 15 depicts a perspective view of an exemplary alternative bracket that may be incorporated into the instrument of FIG. 1.

FIGS. 13-19D show exemplary alternative features that may be incorporated into instrument (10) to promote greater real-time accuracy of visual feedback indicating the longitudinal position of trocar (330) and anvil (400) relative to stapling head assembly. In particular, FIGS. 13-14 show an exemplary alternative indicator member (600) that may be used in place of indicator member (520); while FIG. 15 shows an exemplary alternative bracket (650) that may be used in place of bracket (500).

As shown in FIGS. 13-14, indicator member (600) of this example comprises an upright arm (604), a snap pin (602) projecting laterally from a lower end of arm (604), an indicator needle (606) projecting laterally from an upper end of arm (604), and a coupling pin (608) projecting laterally from an intermediate region of arm (604). Snap pin (602) is configured to snap into a complementary recess provided by a chassis (690) as described below. Indicator needle (606) is positioned to be visible in user feedback feature (114) of handle assembly (110), as described above with respect to indicator needle (526), to thereby visually indicate the pivotal position of indicator member (600), which will indicate the longitudinal position of anvil (400) relative to stapling head assembly (300). Coupling pin (608) is configured to fit in an opening (672) of a flange (670) of bracket (650), as described below. As also described below, this engagement between indicator member (600), chassis (690), and bracket (650) provides pivotal movement of indicator member (600) in response to translation of bracket (650). Unlike indicator member (520) described above, indicator member (600) of the present example comprises a resilient arm (610), which projects upwardly and is resiliently biased to define an oblique angle relative to upright arm (604). As described in greater detail below, resilient arm (610) is configured to interact with chassis (690) to provide a resilient angular bias to indicator member (600).

As shown in FIG. 15, bracket (650) of this example comprises a rigid body (656) that defines a first slot (660) (which is analogous to first slot (504), described above) and a second slot (658) (which is analogous to second slot (506), described above). An upright feature (652) (which is analogous to upright feature (510), described above) is positioned at the proximal end of body (656) and defines an opening (654) (which is analogous to opening (512), described above). Opening (654) is sized to receive trocar actuation rod (220); and upright feature (652) is configured to engage coil spring (170), just like the analogous features of bracket (500) described above. Bracket (650) further includes a laterally presented flange (670), which defines an opening (672). Opening (672) extends between a distal edge (674) and a proximal edge (676).

Figure 16:
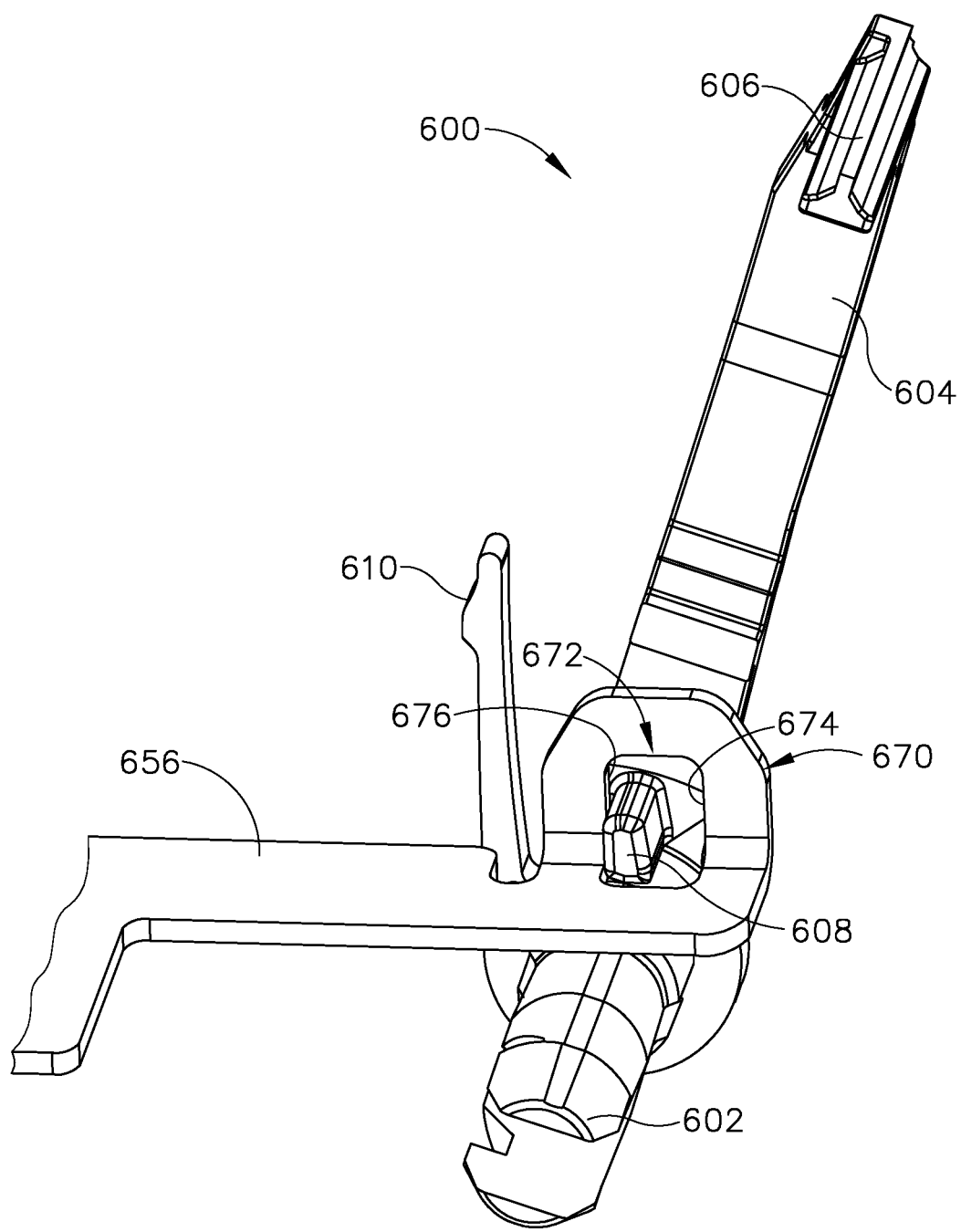
FIG. 16 depicts a perspective view of the indicator member of FIG. 13 in combination with the bracket of FIG. 15.

As shown in FIG. 16, and as noted above, pin (608) is configured to fit in opening (672) of flange (670). The width of opening (672) is larger than the width of pin (608), such that pin (608) cannot contact both edges (674, 676) simultaneously. This structural relationship between the width of opening (672) and the width of pin (608) provides some degree of lost motion between bracket (650) and indicator member (600), as described below with reference to FIGS. 19A-19D.

Figure 17:
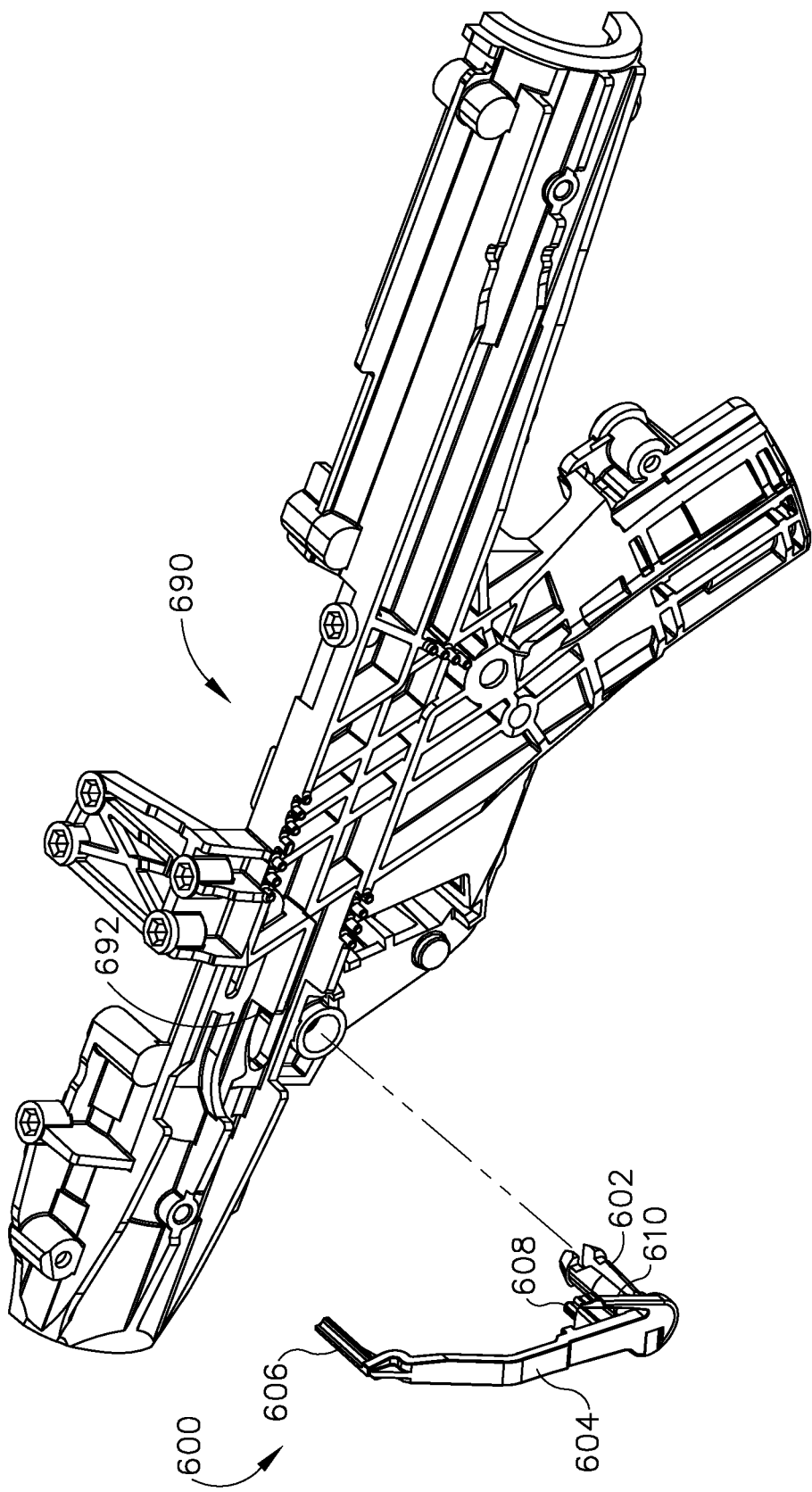
FIG. 17 depicts an exploded perspective view of the indicator member of FIG. 13 with an exemplary alternative chassis that may be incorporated into the instrument of FIG. 1.

FIG. 17 shows an exemplary chassis (690) that may be incorporated into handle assembly (110). Chassis (690) is configured to provide a mechanical ground relative to movable components of handle assembly (110). Chassis (690) of this example comprises a distally presented ridge (692) that is positioned for engagement with resilient arm (610) of indicator member (600). As shown in FIG. 17, snap pin (602) is configured to be inserted into chassis (690). Snap pin (602) thereby secures indicator member (600) to chassis (690) yet permits indicator member (600) to pivot relative to chassis (690) about the longitudinal axis of snap pin (602).

Figure 18A:
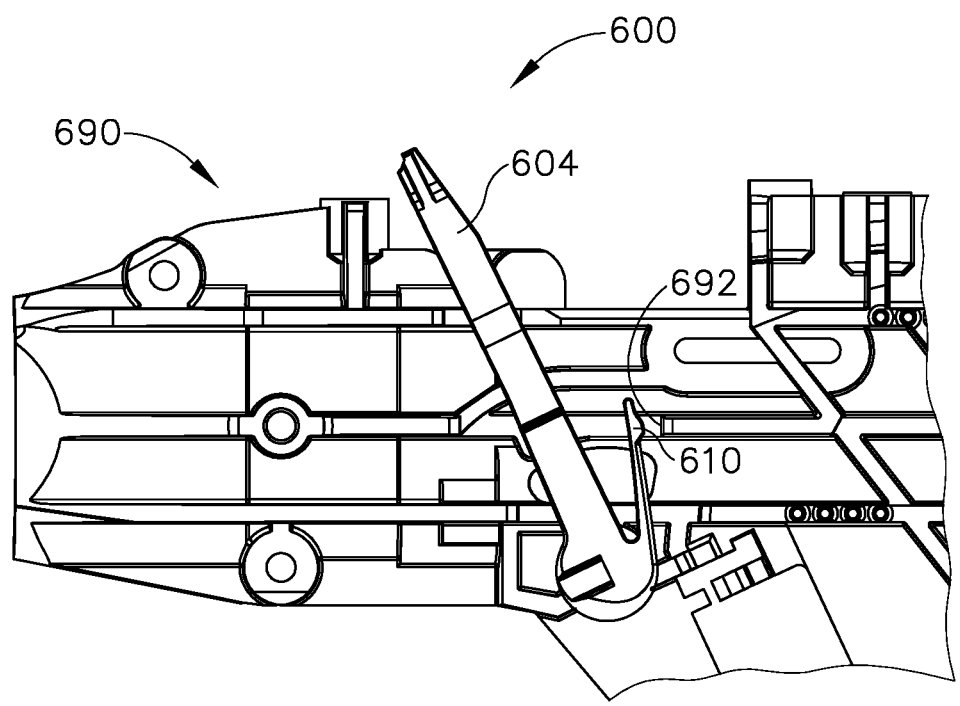
FIG. 18A depicts a side elevational view of the indicator member of FIG. 13 coupled with the chassis of FIG. 17, with the indicator member in a first angular position.

FIGS. 18A-18D show various angular positions of indicator member (600) relative to chassis (690) as trocar (330) and anvil (400) are retracted proximally relative to stapling head assembly (300). In particular, FIG. 18A shows indicator member (600) at a first angular orientation. This first angular orientation would be associated with trocar (330) and anvil (400) being at a furthest distal position relative to stapling head assembly (300). For instance, this orientation may be associated with the operational states depicted in FIGS. 10A and 12B. With indicator member (600) at this first angular orientation, resilient arm (610) is not in contact with ridge (692) of chassis (690), such that a gap is defined between resilient arm (610) and ridge (692).

Figure 18B:
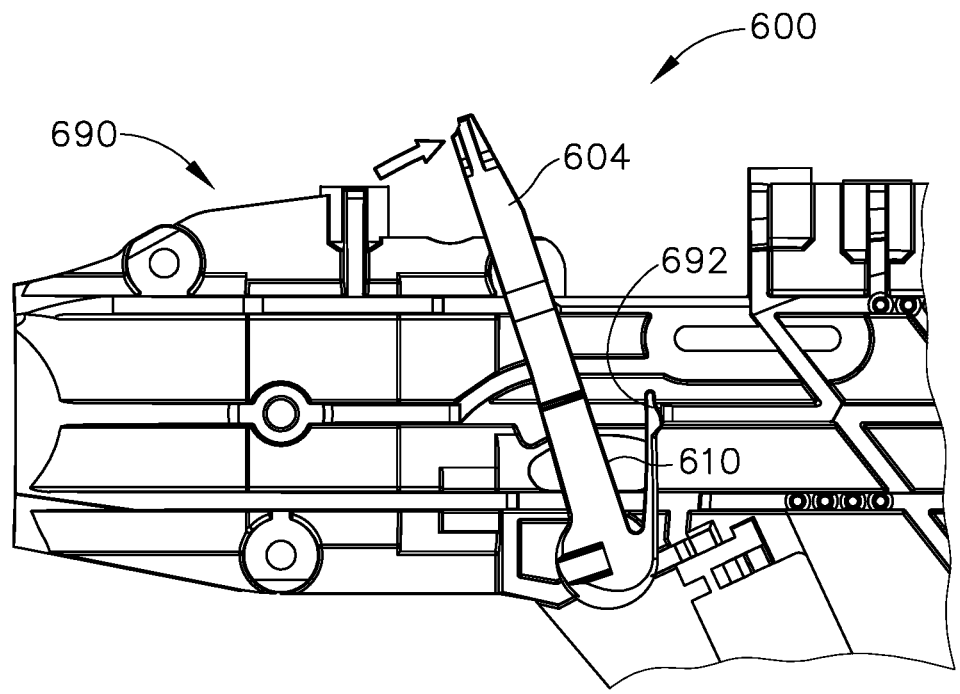
FIG. 18B depicts a side elevational view of the indicator member of FIG. 13 coupled with the chassis of FIG. 17, with the indicator member in a second angular position.
Figure 18C:
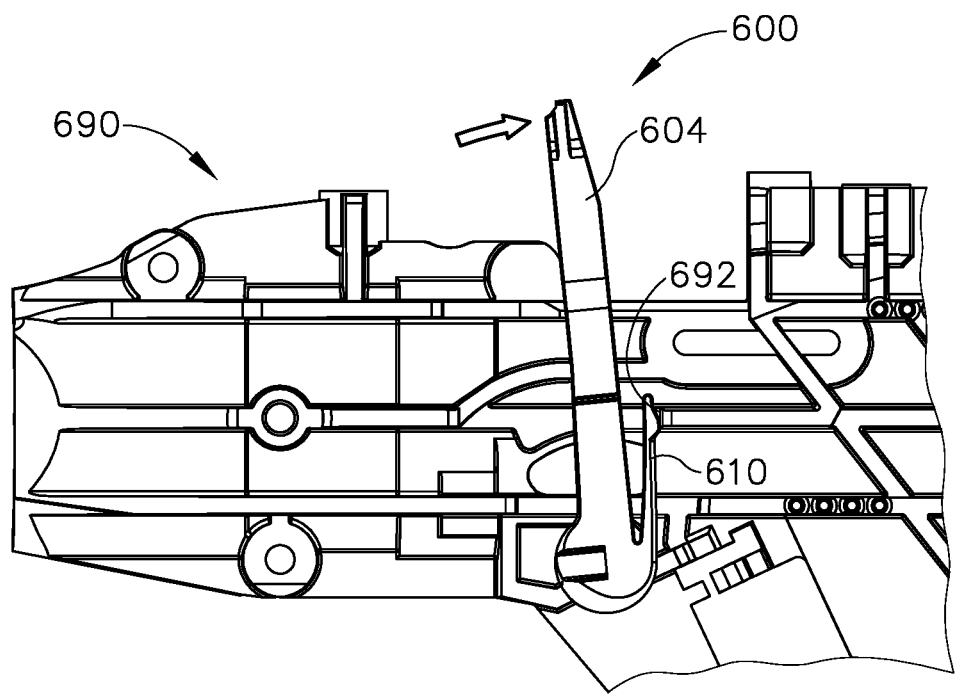
FIG. 18C depicts a side elevational view of the indicator member of FIG. 13 coupled with the chassis of FIG. 17, with the indicator member in a third angular position.
Figure 18D:
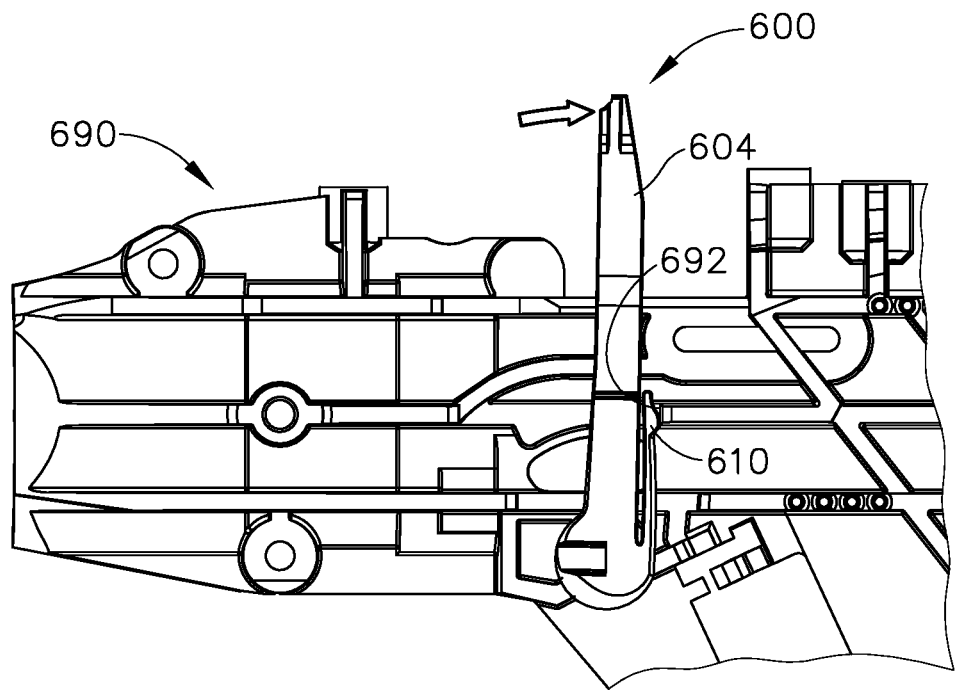
FIG. 18D depicts a side elevational view of the indicator member of FIG. 13 coupled with the chassis of FIG. 17, with the indicator member in a fourth angular position

As the operator rotates knob (130) to retract trocar (330) and anvil (400) proximally relative to stapling head assembly (300), bracket (650) eventually pulls pin (608) proximally, thereby causing indicator member (600) to pivot clockwise (in the view shown in FIGS. 18A-18D) relative to chassis (690). During this clockwise pivotal movement, resilient arm (610) eventually contacts ridge (692) of chassis (690), as shown in FIG. 18B. During the stages shown in FIGS. 18A and 18B, resilient arm (610) is in a non-stressed state. However, as the operator continues to rotate knob (130) to retract trocar (330) and anvil (400) further proximally relative to stapling head assembly (300), bracket (650) continues to pull pin (608) proximally, thereby causing indicator member (600) to pivot clockwise further relative to chassis (690). This results in deformation of resilient arm (610), as shown in FIG. 18C. In the present example, resilient arm (610) contacts ridge (692) and starts deforming before anvil (400) reaches the "green zone" referred to above.

With resilient arm (610) deformed as shown in FIG. 18C, resilient arm (610) is in a stressed state, such that indicator member (600) is resiliently biased in the counterclockwise (in the view shown in FIGS. 18A-18D) direction. Despite the stressed state of resilient arm (610), the operator may continue to rotate knob (130) to retract trocar (330) and anvil (400) further proximally relative to stapling head assembly (300), thereby causing indicator member (600) to pivot clockwise further relative to chassis (690), eventually reaching the state shown in FIG. 18D. At this stage, resilient arm (610) may engage upright arm (604), such that resilient arm (610) may not deform further. In some versions, bracket (650) may not be enabled to translate proximally far enough for resilient arm (610) to ground out against upright arm (604). When the operator reverses rotation of knob (130) to thereby advance anvil (400) distally while resilient arm (610) is in a stressed state, resilient arm (610) will drive indicator member (600) to rotate counterclockwise.

Figure 19A:
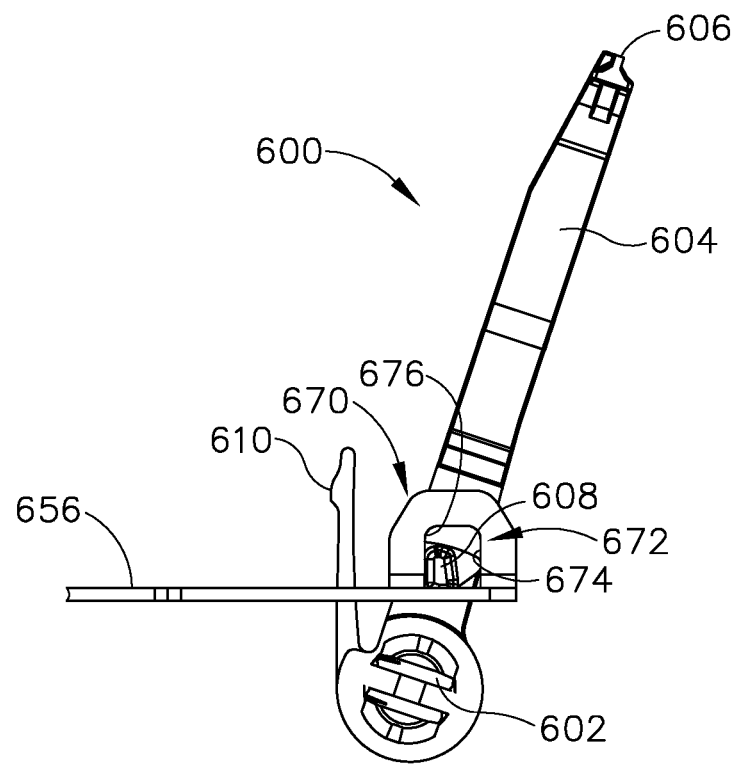
FIG. 19A depicts a side elevational view of the indicator member of FIG. 13 and the bracket of FIG. 15, with the bracket in a first longitudinal position and the indicator member in a first angular position.
Figure 19B:
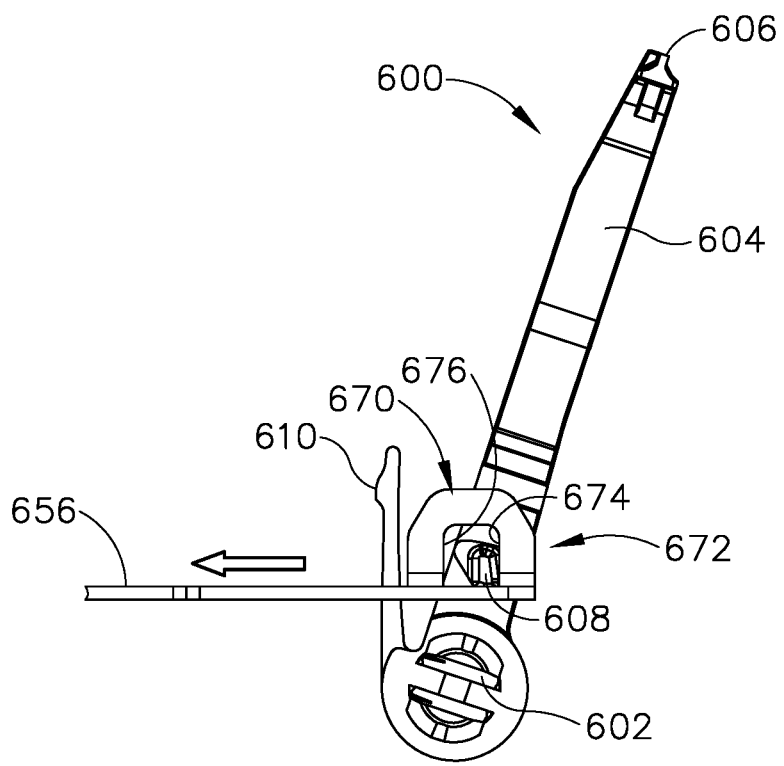
FIG. 19B depicts a side elevational view of the indicator member of FIG. 13 and the bracket of FIG. 15, with the bracket in a second longitudinal position and the indicator member in the first angular position.

As noted above, the structural relationship between the width of opening (672) and the width of pin (608) provides some degree of lost motion between bracket (650) and indicator member (600). This lost motion is shown in FIGS. 19A-19B. FIG. 19A shows bracket (650) in a distal-most position. This operational state corresponds with the operational state shown in FIG. 18A. At this stage, proximal edge (676) of opening (672) is engaged with pin (608); and pin (608) is spaced apart from distal edge (674) of opening (672).

As bracket (650) translates proximally with trocar (330) and anvil (400), bracket (650) eventually reaches the longitudinal position shown in FIG. 19B. At this stage, distal edge (674) of opening (672) is engaged with pin (608); and pin (608) is spaced apart from proximal edge (676) of opening (672). However, during the transition from the stage shown in FIG. 19A to the stage shown in FIG. 19B, indicator member (600) has not pivoted. Indicator member (600) has thus remained stationary while bracket (650) has translated from the position shown in FIG. 19A to the position shown in FIG. 19B. In the context of the stages shown in FIGS. 18A-18D, indicator member (600) would remain in the position shown in FIG. 18A during the stage shown in FIG. 19A and the stage shown in FIG. 19B. In the present example, opening (672) is sized and configured such that pin (608) will not engage distal edge (674) of opening (670) as shown in FIG. 19B until anvil (400) has reached a distance associated with the "green zone" as described above. Moreover, resilient arm (610) will not contact edge (692) until after anvil (400) has reached a distance associated with the "green zone" as described above. Thus, indicator needle (606) will not be positioned proximal to distal-most indicia (552) in user feedback feature (114) until after indicator member (600) has reached the position shown in FIG. 18B, which will not occur until after bracket (650) has reached the position shown in FIG. 19B.

Figure 19C:
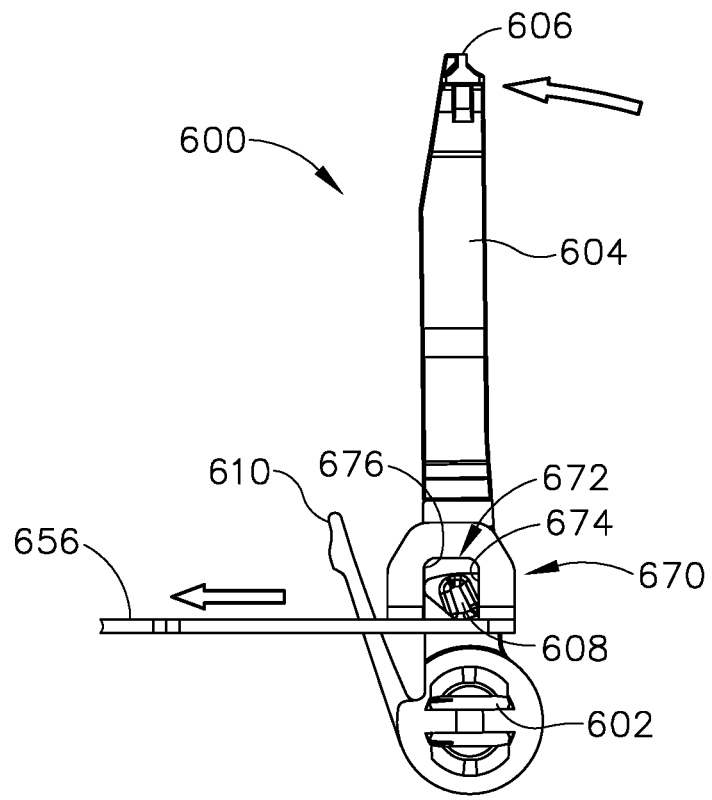
FIG. 19C depicts a side elevational view of the indicator member of FIG. 13 and the bracket of FIG. 15, with the bracket in a third longitudinal position and the indicator member in a second angular position.
Figure 19D:
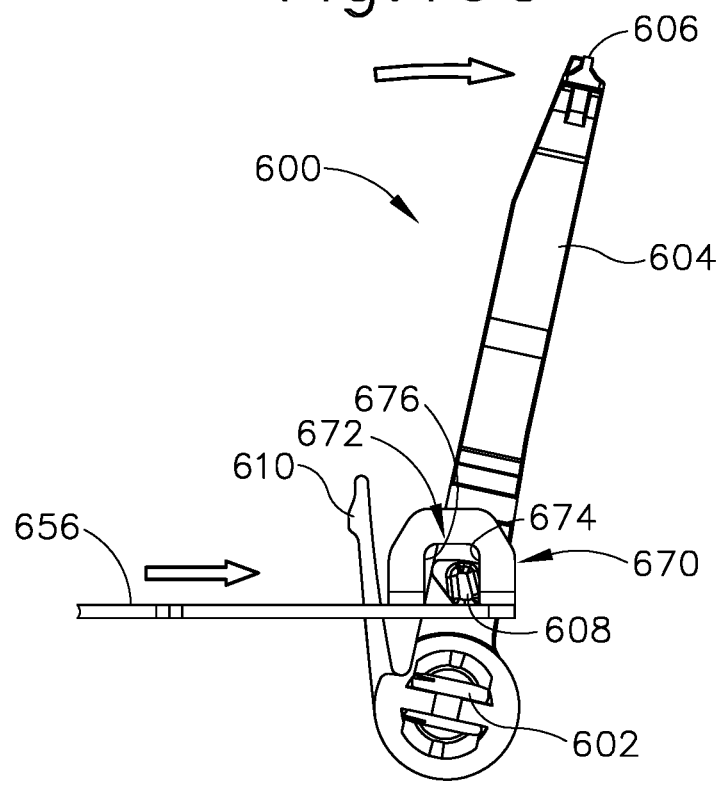
FIG. 19D depicts a side elevational view of the indicator member of FIG. 13 and the bracket of FIG. 15, with the bracket in a fourth longitudinal position and the indicator member in a third angular position.

As bracket (650) continues to translate proximally with trocar (330) and anvil (400), bracket (650) eventually reaches the longitudinal position shown in FIG. 19C. During the range of movement between the stage shown in FIG. 19B and the stage shown in FIG. 19C, At this stage, distal edge (674) of flange (670) bears against pin (608) to drive pin (608) proximally, thereby indicator member (600) to the position shown in FIG. 19C. While chassis (690) is omitted from FIGS. 19A-19D, those of ordinary skill in the art will recognize that resilient arm (610) will be deformed (and thereby stressed) due to engagement between resilient arm (610) and edge (692) during the transition from the stage shown in FIG. 19B and the stage shown in FIG. 19C. Those of ordinary skill in the art will also recognize that the relationship between bracket (650) and indicator member (600) shown in FIG. 19C will be provided throughout the range of motion associated with transitioning among the stages shown in FIGS. 18B-18D.

As noted above, after anastomosis (70) has been formed, or while the operator is adjusting the gap distance (d) between anvil (400) and stapling head assembly (300), the operator may drive trocar (330) and anvil (400) distally. When this occurs, bracket (650) will also translate distally. This will result in movement shown in FIG. 19D. Since bracket (650) is already in a proximal position (e.g., the position shown in FIG. 19C) before such distal movement is initiated, resilient arm (610) is in a stressed state, thereby urging indicator member (600) to pivot distally. Due to this resilient bias, pin (608) remains engaged with distal edge (674) of opening (670) as bracket (650) moves distally. As the operator continues to rotate knob (130) to drive trocar (330) and anvil (400) distally, the distally translating bracket (650) allows resilient arm (610) to drive indicator member (600) back toward the pivotal position shown in FIGS. 19A-19B. After indicator member (600) reaches the pivotal position shown in FIGS. 19A-19B, distal edge (674) disengages pin (608) and bracket (650) may continue to translate distally through a certain range of motion before reaching the longitudinal position shown in FIG. 19A.

In the present example, the lost motion between bracket (650) and indicator (600) between the stage shown in FIG. 19A and the stage shown in FIG. 19B, and the lost motion between resilient arm (610) and edge (692) between the stage shown in FIG. 18A and the stage shown in FIG. 18B, remove hysteresis from movement of indicator arm (600) as trocar (330) and anvil (400) are retracted proximally toward stapling head assembly (300). Likewise, the lost motion between bracket (650) and indicator (600) between the stage shown in FIG. 19B and the stage shown in FIG. 19A, and the lost motion between resilient arm (610) and edge (692) between the stage shown in FIG. 18B and the stage shown in FIG. 18A, remove hysteresis from movement of indicator arm (600) as trocar (330) and anvil (400) are advanced distally away from stapling head assembly (300). During advancement and retraction, this lost motion will occur when anvil (400) is outside of the "green zone" referred to above. Thus, the lost motion will reduce the likelihood that the operator is misled into thinking that anvil (400) is in the "green zone" due to hysteresis that might otherwise keep indicator needle (606) between indicia (552, 556) when anvil (400) is in fact outside of the "green zone."

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly extending distally from the body, wherein the shaft assembly has a distal end; (c) an end effector located at the distal end of the shaft assembly, wherein the end effector comprises: (i) a stationary component, wherein the stationary component is fixedly secured relative to the shaft assembly and is thereby configured to remain stationary relative to the shaft assembly, and (ii) a movable component, wherein the movable component is configured to move relative to the stationary component; and (d) an indicator assembly, wherein the indicator assembly comprises: (i) a translating member, wherein the translating member is configured to translate relative to the body in response to movement of the movable component relative to the stationary component, and (ii) an indicator member, wherein the indicator member is configured to move through a continuum of movement from a first position toward a second position, wherein the indicator member comprises an integral resilient feature, wherein the translating member is configured to drive the indicator member toward the second position in response to movement of the movable component relative to the stationary component in a first direction, wherein the resilient feature is configured to resiliently urge the indicator member toward the first position in response to movement of the movable component relative to the stationary component in a second direction.

Example 2

The apparatus of Example 1, wherein the stationary component comprises a stapling deck, wherein the movable component comprises an anvil, wherein the end effector is operable to drive staples through the deck and toward the anvil.

Example 3

The apparatus of Example 2, wherein the movable component further comprises a trocar, wherein the anvil is coupled with the anvil.

Example 4

The apparatus of any one or more of Examples 2 through 3, wherein the stapling deck is annular, wherein the end effector is operable to drive at least one annular array of staples through the deck and toward the anvil.

Example 5

The apparatus of any one or more of Examples 1 through 4, wherein the movable component is configured to translate linearly relative to the stationary component.

Example 6

The apparatus of Example 5, wherein the end effector defines a longitudinal axis, wherein the movable component is configured to translate linearly along the longitudinal axis.

Example 7

The apparatus of any one or more of Examples 1 through 6, wherein the translating member comprises a plate.

Example 8

The apparatus of Example 7, wherein the plate defines an opening, wherein the indicator member comprises a projection disposed in the opening, wherein the plate is operable to drive the indicator member via the projection.

Example 9

The apparatus of Example 8, wherein the projection has a width, wherein the opening has a width, wherein the width of the opening is greater than the width of the projection, wherein the plate is movable through a first range of motion where the plate does not drive the indicator member via the projection, wherein the plate is movable through a second range of motion where the plate drives the indicator member via the projection.

Example 10

The apparatus of any one or more of Examples 1 through 9, wherein the indicator member is configured to pivot from the first position toward the second position.

Example 11

The apparatus of any one or more of Examples 1 through 10, wherein the integral resilient feature comprises a resilient arm.

Example 12

The apparatus of Example 11, wherein the resilient arm is configured to contact a portion of the body and thereby resiliently bear against the body.

Example 13

The apparatus of Example 12, wherein the indicator member is configured to move from through a first range of motion where the resilient arm does not contact the portion of the body, wherein the indicator member is further configured to move through a second range of motion where the resilient arm contacts the portion of the body.

Example 14

The apparatus of any one or more of Examples 1 through 13, wherein the indicator member comprises an indicator needle, wherein the body comprises a user feedback feature, wherein the indicator needle is configured to move relative to the user feedback feature to thereby visually indicate movement of the movable member in response to the indicator member being driven to move by one or both of the translating member or the resilient feature.

Example 15

The apparatus of Example 14, wherein the user feedback feature further includes indicia indicating a predetermined range of distance between the movable component and the stationary component, wherein the indicator needle is configured to move relative to the indicia to thereby visually indicate positioning of the movable component within the predetermined range of distance relative to the stationary component.

Example 16

An apparatus comprising: (a) a body; (b) a shaft assembly extending distally from the body, wherein the shaft assembly has a distal end; (c) an end effector located at the distal end of the shaft assembly, wherein the end effector comprises: (i) a circular stapling head assembly, wherein the circular stapling head assembly is configured to remain stationary relative to the shaft assembly, (ii) a trocar, wherein the trocar is configured to move relative to the circular stapling head assembly, and (iii) an anvil, wherein the anvil is configured to couple with the trocar, wherein the circular stapling head assembly is configured to drive at least one annular array of staples toward the anvil; and (d) an indicator assembly, wherein the indicator assembly comprises: (i) a plate, wherein the plate is configured to translate relative to the body in response to movement of the trocar and anvil relative to the circular stapling head assembly, and (ii) an indicator member, wherein the indicator member is configured to move relative to the body from a first position toward a second position, wherein the indicator member comprises an integral resilient feature configured to bias the indicator member toward the first position, wherein the plate is configured to drive the indicator member toward the second position in response to movement of the trocar and anvil relative to the circular stapling head assembly in a first direction, wherein the resilient feature is configured to drive the indicator member toward the first position in response to movement of the trocar and anvil relative to the circular stapling head assembly in a second direction.

Example 17

The apparatus of Example 16, wherein the plate defines an opening, wherein the indicator member comprises a projection disposed in the opening, wherein the plate is operable to drive the indicator member via the projection, wherein the projection has a width, wherein the opening has a width, wherein the width of the opening is greater than the width of the projection, wherein the plate is movable through a first range of motion where the plate does not drive the indicator member via the projection, wherein the plate is movable through a second range of motion where the plate drives the indicator member via the projection.

Example 18

The apparatus of any one or more of Examples 16 through 17, wherein the resilient arm is configured to contact a portion of the body and thereby resiliently bear against the body, wherein the indicator member is configured to move from through a first range of motion where the resilient arm does not contact the portion of the body, wherein the indicator member is further configured to move through a second range of motion where the resilient arm contacts the portion of the body.

Example 19

A method of operating a stapler, the method comprising: (a) inserting an end effector of the stapler in a patient, wherein the end effector comprises a circular stapling head assembly and a trocar; (b) coupling an anvil with the trocar; (c) retracting the trocar and anvil proximally through a first range of linear motion, wherein an indicator member of the stapler remains stationary as the trocar and anvil and retract through the first range of linear motion; and (d) retracting the trocar and anvil proximally through a second range of linear motion, wherein the indicator member pivots through a first range of angular motion as the trocar and anvil and retract through the second range of angular motion.

Example 20

The method of Example 19, wherein an integral resilient feature of the indicator member is disengaged from a corresponding feature of a body of the stapler as the trocar and anvil and retract through the first range of linear motion, wherein the integral resilient feature remains disengaged from the corresponding feature of the body as the indicator member pivots through the first range of angular motion, the method further comprising retracting the trocar and anvil proximally through a third range of linear motion, wherein the indicator member pivots through a second range of angular motion as the trocar and anvil and retract through the third range of angular motion, wherein the integral resilient feature engages the corresponding feature of the body as the indicator member pivots through the third range of angular motion, thereby imparting a resilient bias to the indicator member.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. No. 9,572,573 on Feb. 21, 2017, the disclosure of which is incorporated by reference herein; U.S. Pub. No. 2014/0144968, entitled "Surgical Staple with Integral Pledget for Tip Deflection," published May 29, 2014, issued as U.S. Pat. No. 9,289,207 on Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pub. No. 2014/0144969, entitled "Pivoting Anvil for Surgical Circular Stapler," published May 29, 2014, issued as U.S. Pat. No. 9,498,222 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 on Oct. 11, 2016, the disclosure of which is incorporated by reference herein. Various suitable ways in which such teachings may be combined will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
(a) a body;
(b) a shaft assembly extending distally from the body, wherein the shaft assembly has a distal end;
(c) an end effector located at the distal end of the shaft assembly, wherein the end effector comprises:
  (i) a stationary component, wherein the stationary component is fixedly secured relative to the shaft assembly and is thereby configured to remain stationary relative to the shaft assembly, and
  (ii) a movable component, wherein the movable component is configured to move relative to the stationary component; and
(d) an indicator assembly, wherein the indicator assembly comprises:
  (i) a translating member, wherein the translating member is configured to translate relative to the body in response to movement of the movable component relative to the stationary component, and
  (ii) an indicator member, wherein the indicator member is configured to move through a continuum of movement from a first position toward a second position, wherein the indicator member comprises an integral resilient feature,
  wherein the translating member is configured to drive the indicator member toward the second position in response to movement of the movable component relative to the stationary component in a first direction, wherein the resilient feature is configured to resiliently urge the indicator member toward the first position in response to movement of the movable component relative to the stationary component in a second direction.

2. The apparatus of claim 1, wherein the stationary component comprises a stapling deck, wherein the movable component comprises an anvil, wherein the end effector is operable to drive staples through the deck and toward the anvil.

3. The apparatus of claim 2, wherein the movable component further comprises a trocar, wherein the anvil is coupled with the trocar.

4. The apparatus of claim 2, wherein the stapling deck is annular, wherein the end effector is operable to drive at least one annular array of staples through the deck and toward the anvil.

5. The apparatus of claim 1, wherein the movable component is configured to translate linearly relative to the stationary component.

6. The apparatus of claim 5, wherein the end effector defines a longitudinal axis, wherein the movable component is configured to translate linearly along the longitudinal axis.

7. The apparatus of claim 1, wherein the translating member comprises a plate.

8. The apparatus of claim 7, wherein the plate defines an opening, wherein the indicator member comprises a projection disposed in the opening, wherein the plate is operable to drive the indicator member via the projection.

9. The apparatus of claim 8, wherein the projection has a width, wherein the opening has a width, wherein the width of the opening is greater than the width of the projection, wherein the plate is movable through a first range of motion where the plate does not drive the indicator member via the projection, wherein the plate is movable through a second range of motion where the plate drives the indicator member via the projection.

10. The apparatus of claim 1, wherein the indicator member is configured to pivot from the first position toward the second position.

11. The apparatus of claim 1, wherein the integral resilient feature comprises a resilient arm.

12. The apparatus of claim 11, wherein the resilient arm is configured to contact a portion of the body and thereby resiliently bear against the body.

13. The apparatus of claim 12, wherein the indicator member is configured to move from through a first range of motion where the resilient arm does not contact the portion of the body, wherein the indicator member is further configured to move through a second range of motion where the resilient arm contacts the portion of the body.

14. The apparatus of claim 1, wherein the indicator member comprises an indicator needle, wherein the body comprises a user feedback feature, wherein the indicator needle is configured to move relative to the user feedback feature to thereby visually indicate movement of the movable member in response to the indicator member being driven to move by one or both of the translating member or the resilient feature.

15. The apparatus of claim 14, wherein the user feedback feature further includes indicia indicating a predetermined range of distance between the movable component and the stationary component, wherein the indicator needle is configured to move relative to the indicia to thereby visually indicate positioning of the movable component within the predetermined range of distance relative to the stationary component.

16. An apparatus comprising:
(a) a body;
(b) a shaft assembly extending distally from the body, wherein the shaft assembly has a distal end;
(c) an end effector located at the distal end of the shaft assembly, wherein the end effector comprises:
(i) a circular stapling head assembly, wherein the circular stapling head assembly is configured to remain stationary relative to the shaft assembly,
(ii) a trocar, wherein the trocar is configured to move relative to the circular stapling head assembly, and
(iii) an anvil, wherein the anvil is configured to couple with the trocar, wherein the circular stapling head assembly is configured to drive at least one annular array of staples toward the anvil; and
(d) an indicator assembly, wherein the indicator assembly comprises:
(i) a plate, wherein the plate is configured to translate relative to the body in response to movement of the trocar and anvil relative to the circular stapling head assembly, and
(ii) an indicator member, wherein the indicator member is configured to move relative to the body from a first position toward a second position,
wherein the indicator member comprises an integral resilient feature configured to bias the indicator member toward the first position,
wherein the plate is configured to drive the indicator member toward the second position in response to movement of the trocar and anvil relative to the circular stapling head assembly in a first direction,
wherein the resilient feature is configured to drive the indicator member toward the first position in response to movement of the trocar and anvil relative to the circular stapling head assembly in a second direction.

17. The apparatus of claim 16, wherein the plate defines an opening, wherein the indicator member comprises a projection disposed in the opening, wherein the plate is operable to drive the indicator member via the projection, wherein the projection has a width, wherein the opening has a width, wherein the width of the opening is greater than the width of the projection, wherein the plate is movable through a first range of motion where the plate does not drive the indicator member via the projection, wherein the plate is movable through a second range of motion where the plate drives the indicator member via the projection.

18. The apparatus of claim 16, wherein the integral resilient feature is configured to contact a portion of the body and thereby resiliently bear against the body, wherein the indicator member is configured to move from through a first range of motion where the resilient arm does not contact the portion of the body, wherein the indicator member is further configured to move through a second range of motion where the resilient arm contacts the portion of the body.

19. An apparatus comprising:
(a) a body;
(b) a shaft assembly extending distally from the body;
(c) an end effector at a distal end of the shaft assembly, wherein the end effector includes:
(i) a stapling head assembly, and
(ii) an anvil operable to clamp tissue against the stapling head assembly; and (d) an indicator assembly, wherein the indicator assembly includes:
  (i) a moveable member, wherein the movable member is moveable relative to the body in response to approximation of the anvil and the stapling head assembly, and
  (ii) an indicator member, wherein the indicator member is movable relative to the body in a first direction and an opposite second direction, wherein the indicator member includes a resilient feature,
  wherein the movable member is configured to drive the indicator member in the first direction in response to approximation of the anvil and the stapling head assembly,
  wherein the resilient feature is configured to resiliently urge the indicator member in the second direction during distancing of the anvil from the stapling head assembly.

20. The apparatus of claim 19, wherein the first direction comprises a proximal direction, wherein the second direction comprises a distal direction.

* * * * *